ID 007625902B2

United States Patent
Dehmlow et al.

(10) Patent No.: US 7,625,902 B2
(45) Date of Patent: Dec. 1, 2009

(54) IMIDAZOLIDINONE DERIVATIVES

(75) Inventors: Henrietta Dehmlow, Loerrach (DE); Bernd Kuhn, Reinach BL (CH); Ulrike Obst Sander, Reinach BL (CH); Stephan Roever, Inzlingen (DE); Tanja Schulz-Gasch, Liestal (CH); Matthew Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/053,674

(22) Filed: Mar. 24, 2008

(65) Prior Publication Data

US 2008/0242677 A1 Oct. 2, 2008

(30) Foreign Application Priority Data

Mar. 30, 2007 (EP) .................. 07105376

(51) Int. Cl.
*A61K 31/496* (2006.01)
*A61K 31/498* (2006.01)
*C07D 233/32* (2006.01)
*C07D 401/12* (2006.01)
*C07D 403/12* (2006.01)
*C07D 495/04* (2006.01)

(52) U.S. Cl. ............................ 514/252.11; 514/253.04; 514/253.09; 514/254.05; 544/357; 544/362; 544/364; 544/368; 544/370

(58) Field of Classification Search ........................ None
See application file for complete search history.

(56) References Cited

U.S. PATENT DOCUMENTS

2006/0004068 A1 1/2006 Dehmlow et al.

FOREIGN PATENT DOCUMENTS

| WO | WO 00/54759 | 9/2000 |
| WO | WO 01/60818 | 8/2001 |
| WO | WO 02/24632 | 3/2002 |
| WO | WO 03/099769 | 12/2003 |

OTHER PUBLICATIONS

Lund et al., Arterioscler. Thromb. Vasc. Biol. 23, pp. 1169-1177 (2003).
Mitro et al., Nature, 445, pp. 219-223 (2007).
Joseph et al., Curr. Opin. Pharmacol., 3, pp. 192-197 (2003).
Cao et al., J. Biol. Chem., 278, pp. 1131-1136 (2003).
Nadir et al., J. Heterocyclic Chem., 41, pp. 737-739 (2004).

*Primary Examiner*—Emily Bernhardt
(74) *Attorney, Agent, or Firm*—George W. Johnston; Dennis P. Tramaloni; Brian C. Remy

(57) ABSTRACT

The invention is concerned with novel imidazolidinone derivatives of formula (I):

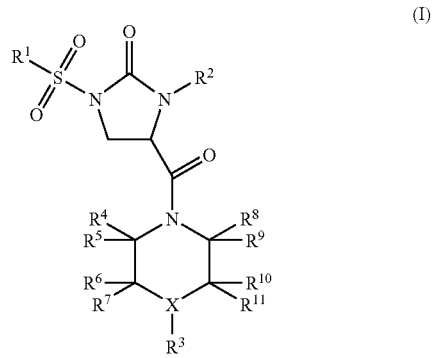

wherein $R^1$ to $R^{11}$ and X are as defined in the description and in the claims, as well as physiologically acceptable salts thereof. These compounds bind to LXR alpha and LXR beta and can be used in pharmaceutical compositions.

24 Claims, No Drawings

IMIDAZOLIDINONE DERIVATIVES

PRIORITY TO RELATED APPLICATION(S)

This application claims the benefit European Patent Application No. 07105376.3, filed Mar. 30, 2007, which is hereby incorporated by reference in its entirety.

BACKGROUND OF THE INVENTION

Liver-X-Receptors (LXRs) are members of the nuclear hormone receptor superfamily. The LXRs are activated by endogenous oxysterols and glucose and regulate the transcription of genes controlling multiple metabolic pathways. Two subtypes, LXRalpha and LXRbeta, have been described (Willy, P. J. et al., Genes Dev. 1995, 9:1033-45; Song, C. et al., Proc Natl Acad Sci USA. 1994, 91:10809-13). LXRbeta is ubiquitously expressed, while LXRalpha is predominantly expressed in cholesterol metabolizing tissues such as the liver, adipose, intestine and macrophage. The LXRs modulate a variety of physiological responses including regulation of cholesterol absorption, cholesterol elimination (bile acid synthesis), and transport of cholesterol from peripheral tissues via plasma lipoproteins to the liver. The LXRs also appear to regulate genes involved in glucose metabolism, cholesterol metabolism in the brain, cellular differentiation and apoptosis, inflammation, and infectious diseases (Geyeregger, R. et al., Cell. Mol. Life. Sci. 2006, 63:524-539.

About half of all patients with coronary artery disease have low concentrations of plasma high-density lipoprotein cholesterol (HDL-C). The atheroprotective function of HDL was first highlighted almost 25 years ago and stimulated exploration of the genetic and environmental factors that influence HDL-C levels (Miller N E., Lipids 1978, 13:914-9). The protective function of HDL derives from its role in a process termed reverse cholesterol transport (Forrester, J. S., and Shah, P. K., Am. J. Cardiol. 2006, 98:1542-49. HDL mediates the removal of cholesterol from cells in peripheral tissues, including macrophage foam cells in the atherosclerotic lesions of the arterial wall. HDL delivers its cholesterol to the liver and sterol-metabolizing organs for conversion to bile and elimination in feces. Studies have shown that HDL-C levels are predictive of coronary artery disease risk independently of low-density lipoprotein cholesterol (LDL-C) levels (Gordon, T. et al., Am J. Med. 1977, 62:707-14).

At present, the estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial unfavorable side-effects limit the therapeutic potential of this approach.

It has been observed that as many as 90% of the 14 million diagnosed type 2 diabetic patients in the United States are overweight or obese, and a high proportion of type 2 diabetic patients have abnormal concentrations of lipoproteins. Studies have shown that the prevalence of total cholesterol >240 mg/dl is 37% in diabetic men and 44% in women. The rates for LDL-C >160 mg/dl are 31% and 44%, and for HDL-C <35 mg/dl are 28% and 11%, in diabetic men and women respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and has been shown to afflict 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in the later stages of the disease, due to exhaustion and failure of pancreatic insulin-producing capacity. Thus, T2D is a cardiovascular-metabolic syndrome associated with multiple co-morbidities, including insulin resistance, dyslipidemia, hypertension, endothelial dysfunction and inflammatory atherosclerosis.

The first line of treatment for dyslipidemia and diabetes at present generally involves a low-fat and low-glucose diet, exercise and weight loss. However, compliance can be moderate, and as the disease progresses, treatment of the various metabolic deficiencies becomes necessary with lipid-modulating agents such as statins and fibrates for dyslipidemia, and hypoglycemic drugs, e.g. sulfonylureas, metformin, or insulin sensitizers of the thiazolidinedione (TZD) class of PPARγ-agonists, for insulin resistance. Recent studies provide evidence that modulators of LXRs would result in compounds with enhanced therapeutic potential, and as such, modulators of LXRs should improve the plasma lipid profile, and raise HDL-C levels (Lund, E. G. et al., Arterioscler. Thromb. Vasc. Biol. 2003, 23:1169-77; Mitro, N. et al., Nature 2007, 445: 219-23). LXRs are also known to control the efflux of cholesterol from the macrophage foam cell of the atherosclerotic lesion, and agonists of LXRs have been shown to be atheroprotective (Joseph, S. B. and Tontonoz, P., Curr. Opin. Pharmacol. 2003, 3:192-7). Thus, modulators of LXRs would be effective treatments for the atherosclerotic disease which underlies the cardiovascular morbidity and mortality of stroke and heart disease. Recent observations also suggest that there is an independent LXR mediated effect on insulin-sensitization in addition to its role in atheroprotection (Cao, G. et al., J Biol. Chem. 2003, 278:1131-6). Thus LXR modulators can also show superior therapeutic efficacy on HDL-raising and atheroprotection, with additional effects on diabetes, compared to current therapies.

Compounds that bind to and activate LXR alpha and LXR beta have previously been suggested (e.g.: WO 03/099769). However, there is still a need for new compounds with improved properties. The present invention provides the novel compounds of formula (I) which bind to LXR alpha and/or LXR beta. The compounds of the present invention unexpectedly exhibit improved pharmacological properties compared to the compounds known in the art, concerning e.g. metabolic stability, selectivity, bioavailability and activity.

SUMMARY OF THE INVENTION

The invention is concerned with the compounds of formula (I):

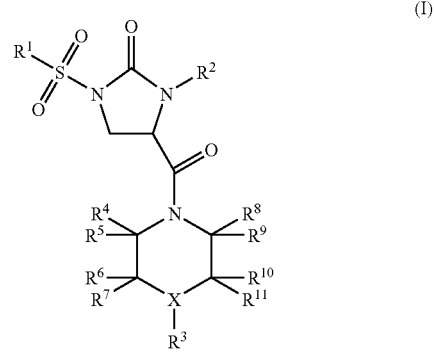

and pharmaceutically acceptable salts thereof, wherein X, and $R^1$-$R^{11}$ are as defined in the detailed description and claims. In addition, the present invention relates to the methods of manufacturing and using the compounds of formula (I) as well as pharmaceutical compositions containing them. The compounds of formula (I) have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. Since multiple facets of combined dyslipidemia and cholesterol homeostasis are addressed by LXR modulators, the novel compounds of the present invention have an enhanced therapeutic potential compared to the compounds already known in the art. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, Alzheimer's disease, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment of infectious diseases such as HIV, cancer and prophylaxis of age-related and inherited (e.g. Stargardt's disease) forms of macular degeneration.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group having one to seven carbon atoms. Preferably the lower group has one to four carbon atom(s).

The term "halogen" refers to fluorine, chlorine, bromine or iodine. Preferably, the halogen is fluorine, chlorine or bromine.

The term "alkyl", alone or in combination with other groups, refers to a branched or straight-chain monovalent saturated aliphatic hydrocarbon radical of one to twenty carbon atoms. Preferably the alkyl has one to sixteen carbon atoms, and more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms. Preferably the lower-alkyl has one to four carbon atoms. This term is further exemplified by such radicals as methyl, ethyl, n-propyl, isopropyl, n-butyl, s-butyl, t-butyl and the like. Lower-alkyl groups can be substituted, for example, by 1 to 5, preferably 1 to 3, halogens. Such a group is referred to as a "halogen-lower-alkyl". Examples of halogen-lower-alkyl groups include chlororethyl and iodopropyl.

The term "fluoro-lower-alkyl" refers to lower-alkyl groups which are mono-substituted or multiply-substituted with fluorine. Examples of fluoro-lower-alkyl groups include $CFH_2$, $CF_2H$, $CF_3$, $CF_3CH_2$, $CF_3(CH_2)_2$, $(CF_3)_2CH$ and $CF_2H—CF_2$.

The term "alkenyl", alone or in combination with other groups, stands for a straight-chain or branched hydrocarbon residue comprising an olefinic bond and up to 20 carbon atoms. Preferably the alkenyl has up to 16 carbon atoms. The term "lower-alkenyl" refers to a straight-chain or branched hydrocarbon residue comprising an olefinic bond and up to 7 carbon atoms. Preferably the lower-alkenyl has up to 4 carbon atoms, such as 2-propenyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two substituents together with the nitrogen atom form a ring. Examples of an amino group include $—NH_2$, methylamino, ethylamino, dimethylamino, diethylamino, methyl-ethylamino, pyrrolidin-1-yl and piperidino etc.

The term "cycloalkyl" refers to a monovalent carbocyclic radical of 3 to 10 carbon atoms. Preferably the cycloalkyl has 3 to 6 carbon atoms, such as cyclopropyl, cyclobutyl, cyclopentyl, and cyclohexyl.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups include $CFH_2$—O, $CF_2H$—O, $CF_3$—O, $CF_3CH_2$—O, $CF_3(CH_2)_2$—O, $(CF_3)_2CH$—O, and $CF_2H—CF_2$—O.

The term "alkylene" refers to a straight chain or branched divalent saturated aliphatic hydrocarbon group of 1 to 20 carbon atoms. Preferably the alkylene has 1 to 16 carbon atoms, and more preferably up to 10 carbon atoms. Lower-alkylene groups as described below also are preferred alkylene groups. The term "lower-alkylene" refers to a straight chain or branched divalent saturated aliphatic hydrocarbon group of 1 to 7 carbon atoms. Preferably the lower-alkylene has 1 to 6 or 3 to 6 carbon atoms. Straight chain alkylene or lower-alkylene groups are preferred.

The term "aryl", alone or in combination with other groups, relates to the phenyl or naphthyl group, preferably the phenyl group, which can optionally be substituted by 1 to 5 (preferably 1 to 3) substituents independently selected from the group consisting of lower-alkyl, lower-alkoxy, halogen, hydroxy, CN, $CF_3$, amino, aminocarbonyl, carboxy, $NO_2$, dioxo-lower-alkylene (forming e.g. a benzodioxyl group), lower-alkylsulfonyl, aminosulfonyl, lower-alkylcarbonyl, lower-alkylcarbonyloxy, lower-alkylcarbonyl-NH, lower-alkoxycarbonyl, fluoro-lower-alkyl, fluoro-lower-alkoxy, lower-alkoxy-lower-alkyl, cycloalkyl and phenyloxy. Naphthyl is also a preferred aryl. Preferred substituents are halogen, lower-alkyl, fluoro-lower-alkyl, CN and lower-alkoxycarbonyl. Furthermore, aryl groups can preferably be substituted as described below in the description and claims.

The term "heterocyclyl", alone or in combination with other groups, signifies a saturated or partially unsaturated 4-membered to 10-membered, monocyclic or bicyclic heterocycle which contains one or more hetero atoms (preferably one to three heteroatoms) selected from nitrogen, oxygen and sulphur. Examples of such heterocyclyl groups include piperidinyl, piperazinyl, pyrrolidinyl, imidazolidinyl, pyrazolidinyl, pyranyl, morpholinyl and oxetanyl. Preferred are piperidinyl and pyranyl. Another preferred heterocyclyl is tetrahydropyranyl. A heterocyclyl group may optionally have a substitution pattern as described earlier in connection with the term "aryl". Furthermore, heterocyclyl groups can preferably be substituted as described below in the description and claims.

The term "heteroaryl" refers to an aromatic 5 to 6 membered monocyclic ring or 9 to 10 membered bicyclic ring which can comprise 1, 2 or 3 atoms selected from nitrogen, oxygen and sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl, 3-thieno[3,2-c]pyridin-4-yl and quinolinyl. Preferred heteroaryl groups are pyridinyl, pyrazinyl and 3-thieno[3,2-c]pyridin-4-yl, particularly pyridinyl. Other preferred heteroaryl are benzo[d]isothiazolyl and benzooxazolyl. A heteroaryl group may optionally have a substitution pattern as described earlier in connection with the term "aryl". Furthermore, heteroaryl groups can preferably be substituted as described below in the description and claims.

The term "leaving group" refers to a group that may be displaced by a nucleophile (e.g. a secondary amine). Typical leaving groups include Cl, Br, I, O—SO$_2$-lower-alkyl (wherein O—SO$_2$—CH$_3$=OMs), O—SO$_2$-fluoro-lower-alkyl (wherein O—SO$_2$—CF$_3$=OTf), O—SO$_2$-aryl (wherein C—SO$_2$-ptolyl=OTs), and O-(para-nitrophenyl).

The term "protecting group" refers to groups which are used to protect functional groups, particularly hydroxy, acid and amino groups, temporarily. Examples of protecting groups are benzyl, p-methoxybenzyl, t-butyl-dimethylsilyl, triethylsilyl, triisopropylsilyl, t-butyl-diphenylsilyl, methyl, ethyl, t-butyl, t-butyloxycarbonyl and benzyloxycarbonyl.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the genus of compounds as defined by the formula.

In detail, the present invention relates to compounds of formula (I):

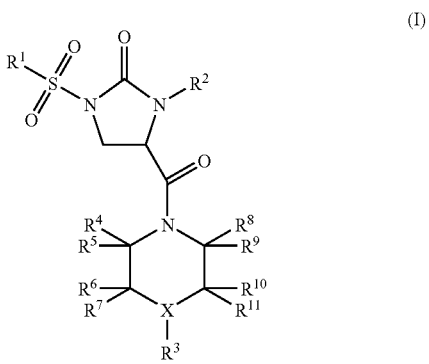

(I)

and pharmaceutically acceptable salts thereof wherein:
X is N or CH;
$R^1$ is selected from the group consisting of:
  (1) lower-alkyl,
  (2) fluoro-lower-alkyl,
  (3) lower-alkoxy-lower-alkyl,
  (4) cycloalkyl,
  (5) cycloalkyl-lower-alkyl,
  (6) aryl,
  (7) aryl-lower-alkyl,
  (8) heterocyclyl,
  (9) heterocyclyl-lower-alkyl,
  (10) heteroaryl, and
  (11) heteroaryl-lower-alkyl,
wherein a cycloalkyl, aryl, heterocyclyl or heteroaryl can optionally be substituted with 1 to 5 substituents independently selected from the group consisting of halogen, lower-alkyl, fluoro-lower-alkyl, lower-alkoxy, lower-alkoxy-lower-alkyl, and fluoro-lower-alkoxy,
$R^2$ is selected from the group consisting of:
  (1) lower-alkyl,
  (2) lower-alkoxy-lower-alkyl,
  (3) halogen-lower-alkyl,
  (4) lower-alkenyl,
  (5) cycloalkyl,
  (6) cycloalkyl-lower-alkyl,
  (7) aryl,
  (8) aryl-lower-alkyl,
  (9) heterocyclyl,
  (10) heterocyclyl-lower-alkyl,
  (11) heteroaryl, and
  (12) heteroaryl-lower-alkyl,
wherein a cycloalkyl, aryl, heterocyclyl or heteroaryl can optionally be substituted with 1 to 5 substituents independently selected from the group consisting of halogen, lower-alkyl, fluoro-lower-alkyl, lower-alkoxy, and fluoro-lower-alkoxy;
$R^3$ is aryl or heteroaryl, wherein said aryl or heteroaryl can optionally be substituted with 1 to 5 substituents independently selected from the group consisting of halogen, CN, lower-alkyl, fluoro-lower-alkyl, lower-alkoxy, and fluoro-lower-alkoxy;
$R^4$, $R^5$, $R^6$, $R^7$, $R^8$, $R^9$, $R^{10}$ and $R^{11}$ independently from each other are hydrogen or lower-alkyl, or $R^4$ and $R^5$ are bound together with the carbon atom to which they are attached to form a ring of 3 to 7 carbon atoms, or $R^6$ and $R^7$ are bound together with the carbon atom to which they are attached to form a ring of 3 to 7 carbon atoms, or $R^8$ and $R^9$ are bound together with the carbon atom to which they are attached to form a ring of 3 to 7 carbon atoms, or $R^{10}$ an $R^{11}$ are bound together with the carbon atom to which they are attached to form a ring of 3 to 7 carbon atoms.

Compounds of formula (I) are individually preferred and physiologically acceptable salts thereof are individually preferred, with the compounds of formula (I) being particularly preferred.

The compounds of formula (I) have one or more asymmetric C atoms and can therefore exist as an enantiomeric mixture, mixture of stereoisomers or as optically pure compounds.

Preferred compounds of the present invention are those, wherein X is N. Other preferred compounds of the present invention are those, wherein $R^1$ is lower-alkyl, fluoro-lower-alkyl or phenyl, which phenyl is optionally substituted with 1 to 3 substituents independently selected from the group consisting of halogen, lower-alkyl, fluoro-lower-alkyl, lower-alkoxy and fluoro-lower-alkoxy. More preferably, $R^1$ is lower-alkyl or phenyl, which phenyl is optionally substituted with 1 to 2 substituents independently selected from the group consisting of halogen and fluoro-lower-alkyl. Even more preferably, $R^1$ is isopropyl, 2-trifluoromethyl-phenyl, 2-chloro-phenyl or 2,3-dichloro-phenyl. Furthermore, it is preferred that $R^1$ is phenyl. Other preferred compounds of formula (I) as described above are those, wherein $R^1$ is pyridinyl, naphthyl, cycloalkyl or cycloalkyl-lower-alkyl, particularly those, wherein $R^1$ is naphthyl.

Another preferred embodiment of the present invention relates to compounds of formula (I) as described above, wherein $R^2$ is lower-alkyl, lower-alkenyl, cycloalkyl or phenyl, which phenyl is optionally substituted with 1 to 3 substituents of halogen. Preferably, $R^2$ is isopropyl, cyclohexyl, phenyl, 2-fluoro-phenyl, 2-chloro-phenyl or 2,4-difluoro-phenyl. Other preferred compounds of formula (I) as described above are those, wherein $R^2$ is halogen-lower-alkyl, tetrahydropyranyl, pyridinyl or aryl-lower-alkyl, particularly those, wherein $R^2$ is benzyl.

Furthermore, it is preferred, that $R^3$ is phenyl or a heteroaryl selected from the group consisting of pyridinyl, 3-thieno[3,2-c]pyridin-4-yl and pyrazinyl, which phenyl or heteroaryl is optionally substituted with 1 to 3 substituents independently selected from the group consisting of halogen, CN, lower-alkyl, fluoro-lower-alkyl and lower-alkoxy. More preferably, $R^3$ is phenyl or pyridinyl, which phenyl or pyridinyl is optionally substituted with 1 to 2 substituents independently selected from the group consisting of halogen, lower-alkyl and fluoro-lower-alkyl. Even more preferably, $R^3$ is 2,5-dimethyl-phenyl, 2-methyl-5-chloro-phenyl, 3-trifluoromethyl-pyridin-2-yl, 3-chloro-pyridin-2-yl or 3-bromo-6-methyl-pyridin-2-yl. Other preferred compounds of formula (I) as described above are those, wherein $R^3$ is a heteroaryl selected from the group consisting of benzo[d]isothiazolyl, benzooxazolyl and pyrazinyl, which heteroaryl is optionally substituted with 1 to 3 substituents of lower-alkyl, particularly those, wherein $R^3$ is benzo[d]isothiazol-3-yl or 3,6-dimethyl-pyrazin-2-yl.

Preferred compounds according to the present invention are those, wherein $R^4$, $R^5$, $R^6$, $R^7$, $R^8$, $R^9$, $R^{10}$ and $R^{11}$ independently are hydrogen or lower-alkyl. Furthermore, it is preferred that at least 4 of $R^4$, $R^5$, $R^6$, $R^7$, $R^8$, $R^9$, $R^{10}$ and $R^{11}$ are hydrogen. It is also preferred that not more than two of —$R^4$-$R^5$—, —$R^6$-$R^7$—, —$R^8$-$R^9$— and —$R^{10}$-$R^{11}$— are bound together to form a ring. Particularly preferred compounds according to the present invention are those, wherein $R^4$, $R^5$, $R^6$, $R^7$, $R^8$, $R^9$, $R^{10}$ and $R^{11}$ are hydrogen.

In particular, preferred compounds are the compounds of formula (I) described in the examples as individual compounds as well as pharmaceutically acceptable salts thereof.

Preferred compounds of formula (I) are those selected from the group consisting of:
(RS)-4-[4-(2,5-Dimethyl-phenyl)-piperazine-1-carbonyl]-1-(3-methoxy-benzenesulfonyl)-3-phenyl-imidazolidin-2-one,
(RS)-1-Benzenesulfonyl-4-[4-(2,5-dimethyl-phenyl)-piperazine-1-carbonyl]-3-phenyl-imidazolidin-2-one,
(RS)-1-(3-Methoxy-benzenesulfonyl)-4-[4-(2-methoxy-phenyl)-piperazine-1-carbonyl]-3-phenyl-imidazolidin-2-one,
(RS)-1-(3-Methoxy-benzenesulfonyl)-3-phenyl-4-[4-(3-trifluoromethyl-phenyl)-piperazine-1-carbonyl]-imidazolidin-2-one,
(RS)-1-(3-Methoxy-benzenesulfonyl)-3-phenyl-4-[4-(3-trifluoromethyl-pyridin-2-yl)-piperazine-1-carbonyl]-imidazolidin-2-one,
(RS)-1-(3-Methoxy-benzenesulfonyl)-4-[4-(3-methyl-pyridin-2-yl)-piperazine-1-carbonyl]-3-phenyl-imidazolidin-2-one,
(RS)-1-(3-Methoxy-benzenesulfonyl)-4-[4-(2-methoxy-phenyl)-piperidine-1-carbonyl]-3-phenyl-imidazolidin-2-one,
(RS)-3-(2-Chloro-phenyl)-4-[4-(2,5-dimethyl-phenyl)-piperazine-1-carbonyl]-1-(3-methoxy-benzenesulfonyl)-imidazolidin-2-one,
(RS)-4-[4-(5-Chloro-2-methyl-phenyl)-piperazine-1-carbonyl]-3-(2-chloro-phenyl)-1-(3-methoxy-benzenesulfonyl)-imidazolidin-2-one,
(RS)-4-[4-(2,5-Dimethyl-phenyl)-piperazine-1-carbonyl]-3-phenyl-1-(toluene-4-sulfonyl)-imidazolidin-2-one,
(RS)-4-[4-(2,5-Dimethyl-phenyl)-piperazine-1-carbonyl]-3-phenyl-1-(2-trifluoromethyl-benzenesulfonyl)-imidazolidin-2-one,
(RS)-4-[4-(5-Chloro-2-methyl-phenyl)-piperazine-1-carbonyl]-3-phenyl-1-(2-trifluoromethyl-benzenesulfonyl)-imidazoidin-2-one,
(RS)-2-{4-[2-Oxo-3-phenyl-1-(2-trifluoromethyl-benzenesulfonyl)-imidazolidine-4-carbonyl]-piperazin-1-yl}-benzonitrile,
(RS)-1-Benzenesulfonyl-4-[4-(2,5-dimethyl-phenyl)-piperazine-1-carbonyl]-3-ethyl-imidazolidin-2-one,
(RS)-1-Benzenesulfonyl-4-[4-(2,5-dimethyl-phenyl)-piperazine-1-carbonyl]-3-isopropyl-imidazolidin-2-one,
(RS)-1-Benzenesulfonyl-4-[4-(2,5-dimethyl-phenyl)-piperazine-1-carbonyl]-3-propyl-imidazolidin-2-one,
(RS)-3-Allyl-1-benzenesulfonyl-4-[4-(2,5-dimethyl-phenyl)-piperazine-1-carbonyl]-imidazolidin-2-one,
(RS)-1-Benzenesulfonyl-3-butyl-4-[4-(2,5-dimethyl-phenyl)-piperazine-1-carbonyl]-imidazolidin-2-one,
(RS)-1-Benzenesulfonyl-3-cyclopentyl-4-[4-(2,5-dimethyl-phenyl)-piperazine-1-carbonyl]-imidazolidin-2-one,
(RS)-1-Benzenesulfonyl-3-cyclohexyl-4-[4-(2,5-dimethyl-phenyl)-piperazine-1-carbonyl]-imidazolidin-2-one,
(S)-1-Benzenesulfonyl-4-[4-(2,5-dimethyl-phenyl)-piperazine-1-carbonyl]-3-phenyl-imidazolidin-2-one,
(R)-1-Benzenesulfonyl-4-[4-(2,5-dimethyl-phenyl)-piperazine-1-carbonyl]-3-phenyl-imidazolidin-2-one,
(S)-1-Benzenesulfonyl-4-[4-(2,5-dimethyl-phenyl)-piperazine-1-carbonyl]-3-(2-fluoro-phenyl)-imidazolidin-2-one, (RS)-1-Benzenesulfonyl-3-(2-chloro-phenyl)-4-[4-(2,5-dimethyl-phenyl)-piperazine-1-carbonyl]-imidazolidin-2-one,
(RS)-1-Benzenesulfonyl-3-(3-chloro-phenyl)-4-[4-(2,5-dimethyl-phenyl)-piperazine-1-carbonyl]-imidazolidin-2-one,
(RS)-1-Benzenesulfonyl-3-(4-chloro-phenyl)-4-[4-(2,5-dimethyl-phenyl)-piperazine-1-carbonyl]-imidazolidin-2-one,
(RS)-1-Benzenesulfonyl-4-[4-(2,5-dimethyl-phenyl)-piperazine-1-carbonyl]-3-(4-fluoro-phenyl)-imidazolidin-2-one,
(S)-1-Benzenesulfonyl-4-[4-(2,5-dimethyl-phenyl)-piperazine-1-carbonyl]-3-(4-fluoro-phenyl)-imidazolidin-2-one,
(S)-1-Benzenesulfonyl-3-(2)-4-difluoro-phenyl)-4-[4-(2,5-dimethyl-phenyl)-piperazine-1-carbonyl]-imidazolidin-2-one,
(RS)-1-Benzenesulfonyl-3-benzyl-4-[4-(2,5-dimethyl-phenyl)-piperazine-1-carbonyl]-imidazolidin-2-one,
(+)-4-[4-(5-Chloro-2-methyl-phenyl)-piperazine-1-carbonyl]-3-(2-chloro-phenyl)-1-(3-methoxy-benzenesulfonyl)-imidazolidin-2-one,
(−)-4-[4-(5-Chloro-2-methyl-phenyl)-piperazine-1-carbonyl]-3-(2-chloro-phenyl)-1-(3-methoxy-benzenesulfonyl)-imidazolidin-2-one,
(RS)-1-(3-Chloro-benzenesulfonyl)-4-[4-(2,5-dimethyl-phenyl)-piperazine-1-carbonyl]-3-phenyl-imidazolidin-2-one,
(RS)-1-(2-Chloro-benzenesulfonyl)-4-[4-(2,5-dimethyl-phenyl)-piperazine-1-carbonyl]-3-phenyl-imidazolidin-2-one,
(RS)-1-(2,4-Difluoro-benzenesulfonyl)-4-[4-(2,5-dimethyl-phenyl)-piperazine-1-carbonyl]-3-phenyl-imidazolidin-2-one,
(RS)-4-[4-(2,5-Dimethyl-phenyl)-piperazine-1-carbonyl]-3-phenyl-1-(3,3,3-trifluoro-propane-1-sulfonyl)-imidazolidin-2-one,
(RS)-4-[4-(2,5-Dimethyl-phenyl)-piperazine-1-carbonyl]-3-phenyl-1-(propane-2-sulfonyl)-imidazolidin-2-one,
(RS)-1-(Butane-1-sulfonyl)-4-[4-(2,5-dimethyl-phenyl)-piperazine-1-carbonyl]-3-phenyl-imidazolidin-2-one,
(RS)-1-Benzenesulfonyl-3-cyclohexyl-4-[4-(3-trifluoromethyl-pyridin-2-yl)-piperazine-1-carbonyl]-imidazolidin-2-one,
(RS)-1-Benzenesulfonyl-4-[4-(3-chloro-5-trifluoromethyl-pyridin-2-yl)-piperazine-1-carbonyl]-3-cyclohexyl-imidazolidin-2-one,
(RS)-2-[4-(1-Benzenesulfonyl-3-cyclohexyl-2-oxo-imidazolidine-4-carbonyl)-piperazin-1-yl]-nicotinonitrile,
(RS)-1-Benzenesulfonyl-3-cyclohexyl-4-(4-pyridin-2-yl-piperazine-1-carbonyl)-imidazolidin-2-one,
(RS)-1-Benzenesulfonyl-3-cyclohexyl-4-[4-(5-trifluoromethyl-pyridin-2-yl)-piperazine-1-carbonyl]-imidazolidin-2-one,
(RS)-1-Benzenesulfonyl-3-cyclohexyl-4-[4-(6-methyl-pyridin-2-yl)-piperazine-1-carbonyl]-imidazolidin-2-one,
(RS)-6-[4-(1-Benzenesulfonyl-3-cyclohexyl-2-oxo-imidazolidine-4-carbonyl)-piperazin-1-yl]-nicotinonitrile,
(RS)-1-Benzenesulfonyl-3-cyclohexyl-4-[4-thieno[3,2-c]pyridin-4-yl-piperazine-1-carbonyl)-imidazolidin-2-one,
(RS)-1-Benzenesulfonyl-3-cyclohexyl-4-[4-(3,5-dichloro-pyridin-2-yl)-piperazine-1-carbonyl)-imidazolidin-2-one,
(RS)-3-Phenyl-1-(2-trifluoromethyl-benzenesulfonyl)-4-[4-(3-trifluoromethyl-pyridin-2-yl)-piperazine-1-carbonyl]-imidazolidin-2-one,
(RS)-1-Benzenesulfonyl-3-(2-chloro-phenyl)-4-[4-(3-trifluoromethyl-pyridin-2-yl)-piperazine-1-carbonyl]-imidazolidin-2-one,
(S)-1-Benzenesulfonyl-3-(2-chloro-phenyl)-4-[4-(2,5-dimethyl-phenyl)-piperazine-1-carbonyl]-imidazolidin-2-one,
(RS)-4-[4-(3-Chloro-5-trifluoromethyl-pyridin-2-yl)-piperazine-1-carbonyl]-3-phenyl-1-(2-trifluoromethyl-benzenesulfonyl)-imidazolidin-2-one,
(RS)-1-Benzenesulfonyl-4-[4-(3-bromo-6-methyl-pyridin-2-yl)-piperazine-1-carbonyl]-3-cyclohexyl-imidazolidin-2-one,
(RS)-1-Benzenesulfonyl-3-cyclohexyl-4-[4-(4-methyl-pyridin-2-yl)-piperazine-1-carbonyl]-imidazolidin-2-one,
(RS)-2-[4-(1-Benzenesulfonyl-3-cyclohexyl-2-oxo-imidazolidine-4-carbonyl)-piperazin-1-yl]-6-methyl-nicotinonitrile,
(RS)-1-(2,3-Dichloro-benzenesulfonyl)-4-[4-(2,5-dimethyl-phenyl)-piperazine-1-carbonyl]-3-phenyl-imidazolidin-2-one,
(RS)-1-(2,5-Dichloro-benzenesulfonyl)-4-[4-(2,5-dimethyl-phenyl)-piperazine-1-carbonyl]-3-phenyl-imidazolidin-2-one,
(RS)-4-[4-(2,5-Dimethyl-phenyl)-piperazine-1-carbonyl]-1-(2-fluoro-benzenesulfonyl)-3-phenyl-imidazolidin-2-one,
(RS)-4-[4-(2,5-Dimethyl-phenyl)-piperazine-1-carbonyl]-1-(3-fluoro-benzenesulfonyl)-3-phenyl-imidazolidin-2-one,
(RS)-1-(3-Chloro-2-fluoro-benzenesulfonyl)-4-[4-(2,5-dimethyl-phenyl)-piperazine-1-carbonyl]-3-phenyl-imidazolidin-2-one,
(RS)-1-(3-Difluoromethoxy-benzenesulfonyl)-4-[4-(2,5-dimethyl-phenyl)-piperazine-1-carbonyl]-3-phenyl-imidazolidin-2-one,
(RS)-4-[4-(2,5-Dimethyl-phenyl)-piperazine-1-carbonyl]-3-phenyl-1-(3-trifluoromethyl-benzenesulfonyl)-imidazolidin-2-one,
(RS)-1-Benzenesulfonyl-3-cyclohexyl-4-(3',6'-dimethyl-2,3,5,6-tetrahydro-[1,2']bipyrazinyl-4-carbonyl)-imidazolidin-2-one,
(RS)-1-Benzenesulfonyl-3-(2-chloro-phenyl)-4-[4-(3-chloro-pyridin-2-yl)-piperazine-1-carbonyl]-imidazolidin-2-one,
(RS)-1-(2,5-Difluoro-benzenesulfonyl)-4-[4-(2,5-dimethyl-phenyl)-piperazine-1-carbonyl]-3-phenyl-imidazolidin-2-one,
(RS)-1-(2,6-Dichloro-benzenesulfonyl)-4-[4-(2,5-dimethyl-phenyl)-piperazine-1-carbonyl]-3-phenyl-imidazolidin-2-one,
(S)-1-benzenesulfonyl-3-benzyl-4-[4-(2,5-dimethyl-phenyl)-piperazine-1-carbonyl]-imidazolidin-2-one, and pharmaceutically acceptable salts thereof.

Particularly preferred compounds of formula (I) are those selected from the group consisting of:
(RS)-4-[4-(2,5-Dimethyl-phenyl)-piperazine-1-carbonyl]-3-phenyl-1-(2-trifluoromethyl-benzenesulfonyl)-imidazolidin-2-one,
(RS)-4-[4-(5-Chloro-2-methyl-phenyl)-piperazine-1-carbonyl]-3-phenyl-1-(2-trifluoromethyl-benzenesulfonyl)-imidazolidin-2-one,
(RS)-1-Benzenesulfonyl-4-[4-(2,5-dimethyl-phenyl)-piperazine-1-carbonyl]-3-isopropyl-imidazolidin-2-one,
(S)-1-Benzenesulfonyl-4-[4-(2,5-dimethyl-phenyl)-piperazine-1-carbonyl]-3-(2-fluoro-phenyl)-imidazolidin-2-one,
(S)-1-Benzenesulfonyl-3-(2,4-difluoro-phenyl)-4-[4-(2,5-dimethyl-phenyl)-piperazine-1-carbonyl]-imidazolidin-2-one,
(RS)-1-(2-Chloro-benzenesulfonyl)-4-[4-(2,5-dimethyl-phenyl)-piperazine-1-carbonyl]-3-phenyl-imidazolidin-2-one,
(RS)-4-[4-(2,5-Dimethyl-phenyl)-piperazine-1-carbonyl]-3-phenyl-1-(propane-2-sulfonyl)-imidazolidin-2-one, (RS)-1-Benzenesulfonyl-3-cyclohexyl-4-[4-(3-trifluoromethyl-pyridin-2-yl)-piperazine-1-carbonyl]-imidazolidin-2-one,
(RS)-1-Benzenesulfonyl-3-(2-chloro-phenyl)-4-[4-(3-trifluoromethyl-pyridin-2-yl)-piperazine-1-carbonyl]-imidazolidin-2-one,
(S)-1-Benzenesulfonyl-3-(2-chloro-phenyl)-4-[4-(2,5-dimethyl-phenyl)-piperazine-1-carbonyl]-imidazolidin-2-one,
(RS)-1-Benzenesulfonyl-4-[4-(3-bromo-6-methyl-pyridin-2-yl)-piperazine-1-carbonyl]-3-cyclohexyl-imidazolidin-2-one,
(RS)-1-(2,3-Dichloro-benzenesulfonyl)-4-[4-(2,5-dimethyl-phenyl)-piperazine-1-carbonyl]-3-phenyl-imidazolidin-2-one,
(RS)-1-Benzenesulfonyl-3-(2-chloro-phenyl)-4-[4-(3-chloro-pyridin-2-yl)-piperazine-1-carbonyl]-imidazolidin-2-one, and pharmaceutically acceptable salts thereof.

Other preferred compounds of formula (I) are those selected from the group consisting of
(RS)-1-Benzenesulfonyl-4-(4-benzo[d]isothiazol-3-yl-piperazine-1-carbonyl)-3-(2-chloro-phenyl)-imidazolidin-2-one,
(RS)-1-Benzenesulfonyl-4-(4-benzooxazol-2-yl-piperazine-1-carbonyl)-3-(2-chloro-phenyl)-imidazolidin-2-one,
4-[4-(2,5-Dimethyl-phenyl)-piperazine-1-carbonyl]-3-phenyl-1-(pyridine-2-sulfonyl)-imidazolidin-2-one,
(S)-1-(2-Chloro-benzenesulfonyl)-3-(2-chloro-phenyl)-4-[4-(2,5-dimethyl-phenyl)-piperazine-1-carbonyl]-imidazolidin-2-one,
(S)-1-(2-Chloro-benzenesulfonyl)-3-(2-chloro-phenyl)-4-[4-(3-trifluoromethyl-pyridin-2-yl)-piperazine-1-carbonyl]-imidazolidin-2-one,
(S)-1-(2-Chloro-benzenesulfonyl)-3-propyl-4-[4-(3-trifluoromethyl-pyridin-2-yl)-piperazine-1-carbonyl]-imidazolidin-2-one,
1-Benzenesulfonyl-3-cyclohexyl-4-[(R)-2-methyl-4-(3-trifluoromethyl-pyridin-2-yl)-piperazine-1-carbonyl]-imidazolidin-2-one,
1-Benzenesulfonyl-3-cyclohexyl-4-[(S)-2-methyl-4-(3-trifluoromethyl-pyridin-2-yl)-piperazine-1-carbonyl]-imidazolidin-2-one,
(S)-1-(2-Chloro-benzenesulfonyl)-3-isopropyl-4-[4-(3-trifluoromethyl-pyridin-2-yl)-piperazine-1-carbonyl]-imidazolidin-2-one,
(S)-3-Butyl-1-(2-chloro-benzenesulfonyl)-4-[4-(3-trifluoromethyl-pyridin-2-yl)-piperazine-1-carbonyl]-imidazolidin-2-one,
(S)-1-Benzenesulfonyl-4-[4-(2,5-dimethyl-phenyl)-piperazine-1-carbonyl]-3-(3-iodo-propyl)-imidazolidin-2-one,
(S)-1-(2-Chloro-benzenesulfonyl)-3-cyclopropyl-4-[4-(3-trifluoromethyl-pyridin-2-yl)-piperazine-1-carbonyl]-imidazolidin-2-one,
(S)-1-(2-Chloro-benzenesulfonyl)-3-(tetrahydro-pyran-4-yl)-4-[4-(3-trifluoromethyl-pyridin-2-yl)-piperazine-1-carbonyl]-imidazolidin-2-one,
(RS)-4-(3',6'-Dimethyl-2,3,5,6-tetrahydro-[1,2']bipyrazinyl-4-carbonyl)-3-phenyl-1-(2-trifluoromethyl-benzenesulfonyl)-imidazolidin-2-one,
(RS)-1-Benzenesulfonyl-3-(2-chloro-phenyl)-4-(3',6'-dimethyl-2,3,5,6-tetrahydro-[1,2']bipyrazinyl-4-carbonyl)-imidazolidin-2-one,
(RS)-3-(2,4-Difluoro-phenyl)-4-[4-(2,5-dimethyl-phenyl)-piperazine-1-carbonyl]-1-(propane-2-sulfonyl)-imidazolidin-2-one,
(RS)-3-(2,4-Difluoro-phenyl)-4-(3',6'-dimethyl-2,3,5,6-tetrahydro-[1,2']bipyrazinyl-4-carbonyl)-1-(propane-2-sulfonyl)-imidazolidin-2-one,
(RS)-4-[4-(3-Chloro-pyridin-2-yl)-piperazine-1-carbonyl]-3-(2,4-difluoro-phenyl)-1-(propane-2-sulfonyl)-imidazolidin-2-one,
(RS)-3-(2-Chloro-phenyl)-4-[4-(2,5-dimethyl-phenyl)-piperazine-1-carbonyl]-1-(propane-2-sulfonyl)-imidazolidin-2-one,
(RS)-3-(2-Chloro-phenyl)-4-(3',6'-dimethyl-2,3,5,6-tetrahydro-[1,2']bipyrazinyl-4-carbonyl)-1-(propane-2-sulfonyl)-imidazolidin-2-one,
(RS)-3-(2-Chloro-phenyl)-4-[4-(3-chloro-pyridin-2-yl)-piperazine-1-carbonyl]-1-(propane-2-sulfonyl)-imidazolidin-2-one,
(S)-3-Benzyl-4-[4-(2,5-dimethyl-phenyl)-piperazine-1-carbonyl]-1-(naphthalene-1-sulfonyl)-imidazolidin-2-one,
(S)-4-[4-(2,5-Dimethyl-phenyl)-piperazine-1-carbonyl]-1-(naphthalene-1-sulfonyl)-3-propyl-imidazolidin-2-one,
(S)-1-Benzenesulfonyl-4-[4-(2,5-dimethyl-phenyl)-piperazine-1-carbonyl]-3-pyridin-2-yl-imidazolidin-2-one,
(S)-3-Benzyl-1-cyclopropanesulfonyl-4-[4-(2,5-dimethyl-phenyl)-piperazine-1-carbonyl]-imidazolidin-2-one,
(S)-3-Benzyl-1-(cyclohexylmethanesulfonyl)-4-[4-(2,5-dimethyl-phenyl)-piperazine-1-carbonyl]-imidazolidin-2-one,
(S)-1-(Cyclohexylmethanesulfonyl)-4-[4-(2,5-dimethyl-phenyl)-piperazine-1-carbonyl]-3-phenyl-imidazolidin-2-one, and pharmaceutically acceptable salts thereof.

Other particularly preferred compounds of formula (I) are those selected from the group consisting of:
(RS)-1-Benzenesulfonyl-4-(4-benzo[d]isothiazol-3-yl-piperazine-1-carbonyl)-3-(2-chloro-phenyl)-imidazolidin-2-one,
(S)-1-(2-Chloro-benzenesulfonyl)-3-(2-chloro-phenyl)-4-[4-(2,5-dimethyl-phenyl)-piperazine-1-carbonyl]-imidazolidin-2-one,
(S)-1-(2-Chloro-benzenesulfonyl)-3-(2-chloro-phenyl)-4-[4-(3-trifluoromethyl-pyridin-2-yl)-piperazine-1-carbonyl]-imidazolidin-2-one,
(RS)-4-(3',6'-Dimethyl-2,3,5,6-tetrahydro-[1,2']bipyrazinyl-4-carbonyl)-3-phenyl-1-(2-trifluoromethyl-benzenesulfonyl)-imidazolidin-2-one,
(RS)-3-(2-Chloro-phenyl)-4-[4-(2,5-dimethyl-phenyl)-piperazine-1-carbonyl]-1-(propane-2-sulfonyl)-imidazolidin-2-one,
(S)-3-Benzyl-4-[4-(2,5-dimethyl-phenyl)-piperazine-1-carbonyl]-1-(naphthalene-1-sulfonyl)-imidazolidin-2-one, and pharmaceutically acceptable salts thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises a) reacting a compound of formula (II)

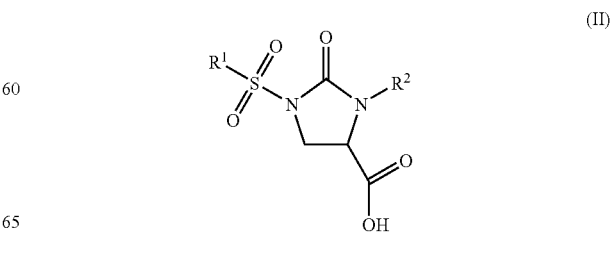

(II)

with a compound of formula (III)

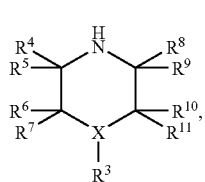

or b) reacting a compound of formula (IV)

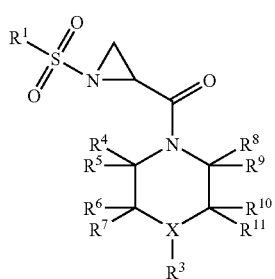

with a compound $R^2NCO$, or c) reacting a compound of formula (V)

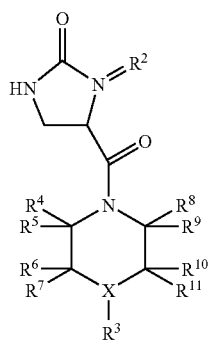

with a compound $R^1SO_2Cl$, or d) reacting a compound of formula (VI)

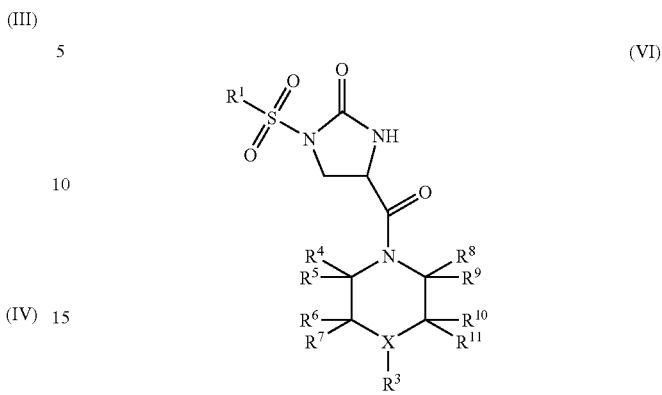

with a compound $R^2LG$, wherein $R^1, R^2, R^3, R^4, R^5, R^6, R^7, R^8, R^9, R^{10}, R^{11}$ and X are as defined above for formula (I) and LG is a leaving group.

The reactions given above can be carried out under conditions well known to the person skilled in the art, e.g. as described below in context with schemes 1, 2, 3 and 4.

The present invention also relates to compounds of formula (I) as defined above, when prepared by a process as described above.

The compounds of formula (I) can be prepared by methods known in the art or as described below. Unless otherwise indicated, the substituents $R^1, R^2, R^3, R^4, R^5, R^6, R^7, R^8, R^9, R^{10}, R^{11}$ and X are as described above for formula (I).

The compounds of formula (I) can be prepared by methods known in the art or as described below in schemes 1 to 4. All starting materials are either commercially available, described in the literature or can be prepared by methods well known in the art. Unless otherwise indicated, $R^1, R^2, R^3, R^4, R^5, R^6, R^7, R^8, R^9, R^{10}, R^{11}$ and X are as described above.

As will be understood by those skilled in the art, for the preparation of enantiomerically pure products, enantiomerically pure starting materials should be used. In addition the compounds of formula I might be separated into the enantiomerically pure compounds by chromatography on a chiral HPLC column, chromatography with a chiral eluant or by crystallization via diastereomeric salts.

Scheme 1 (Method A)

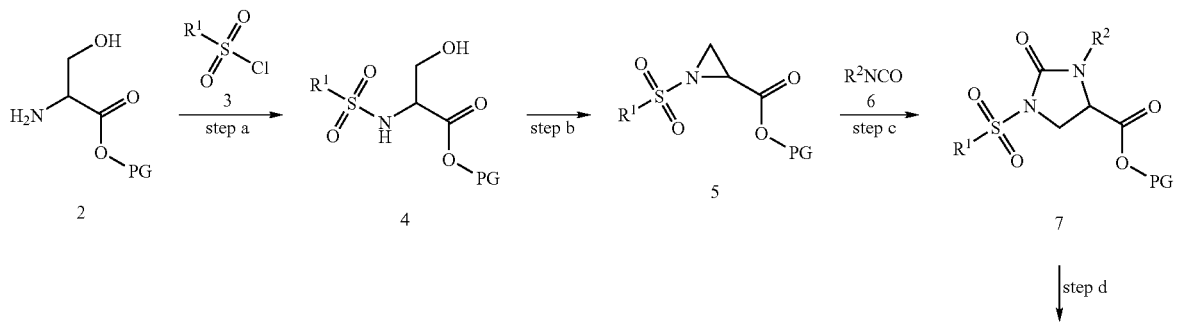

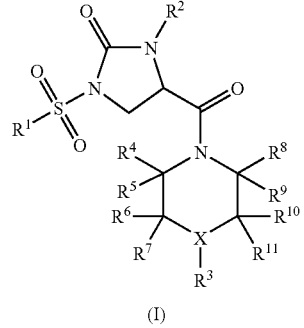
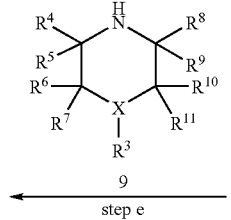
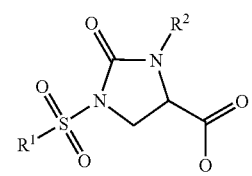

Compounds of formula (I) can be prepared according to the methods described in scheme 1: Appropriately protected serine 2, either in racemic or in enantiomerically pure form, as well as sulfonyl chlorides 3 are either commercially available, described in the literature or can be prepared by methods well known to a person skilled in the art. Sulfonylation of 2 can be achieved by treatment with sulfonyl chlorides 3 in solvents such as dichloromethane, tetrahydrofuran, N,N-dimethylacetamide or dioxane in the presence of bases such as N-ethyl-diisopropylamine, triethylamine or pyridine optionally in the presence of DMAP at 0° C. to room temperature (step a). Mitsunobu reaction of 4, that means treatment with a dialkylazodicarboxylate such as diethylazodicarboxylate, diisopropylazodicarboxylate or di-tert-butyldiazodicarboxylate and with triphenylphosphine in a solvent such as tetrahydrofuran at 0° C. to room temperature, leads to the formation of an aziridine 5 (step b). Alternatively, the hydroxy group of 4 can be converted into a leaving group by treatment with a sulfonylchloride such as methylsulfonyl chloride or tosyl chloride in the presence of a base such as N-ethyl-diisopropylamine, triethylamine or pyridine in a solvent such as dichloromethane or tetrahydrofuran at 0° C. to room temperature. Subsequent treatment with a base such as NaH, triethylamine or N-ethyl-diisopropylamine in a solvent such as tetrahydrofuran or N,N-dimethylacetamide at a temperature from 0° C. to reflux can give the aziridine 5. Treatment of 5 with an isocyanate 6 (either commercially available or described in the literature or prepared by methods well known to a person skilled in the art) in the presence of a metal halide such as sodium iodide or magnesium bromide in a solvent such as tetrahydrofuran or dioxane at temperatures between 0° C. and room temperature gives the sulfonyl-imidazolidinone 7 (step c). The protecting group (PG) of compound 7 can be cleaved in the case of methyl and ethyl esters by treatment with sodium hydroxide or lithium hydroxide in a solvent such as water, methanol, ethanol, tetrahydrofuran or mixtures thereof at temperatures between 0° C. and 60° C. Tert-butyl esters can be cleaved under acidic conditions such as trifluoroacetic acid, HCl or formic acid in solvents such as dichloromethane, tetrahydrofuran or dioxane at temperatures between 0° C. and 60° C. Benzyl esters can be cleaved by hydrogenation in solvents such as methanol, ethanol or ethyl acetate using Pd/C as a catalyst to give acid 8 (step d). For more information on protecting groups see T. W. Greene, P. G. M. Wuts "Protective groups in organic synthesis" Second Edition, John Wiley & Sons, 1991. Condensation of the carboxylic acid 8 and the amine 9 can be achieved by well known procedures for amide formation, such as the use of N-(3-dimethylaminopropyl)-N'-ethyl-carbodiimide-hydrochloride (EDCI), O-(1,2-dihydro-2-oxo-1-pyridyl)-N,N,N,N-tetra-methyluronium-tetrafluorborate (TPTU), O-(7-azabenzotriazol-1-yl)-1,1,3,3-tetramethyluronium hexafluorophosphate (HATU) or benzotriazol-1-yloxytris(dimethylamino)phosphonium hexafluorophoshate (BOP) or other coupling reagents in the presence of a base such as ethyl-diisopropyl-amine, triethylamine, N-methylmorpholine optionally in the presence of 4-dimethylamino-pyridine or 1-hydroxybenzo-triazole (HOBt) in solvents such as tetrahydrofuran, dichloromethane, dimethylformamide, dimethylacetamide or dioxane at temperatures between 0° C. and ambient temperature (step e). Alternatively, a two-step procedure might be used: treatment of the acid 8 with oxalyl chloride in $CH_2Cl_2$ in the presence of DMF or with thionyl chloride in toluene, followed by reaction with the amine 9.

Scheme 2: (Method B)

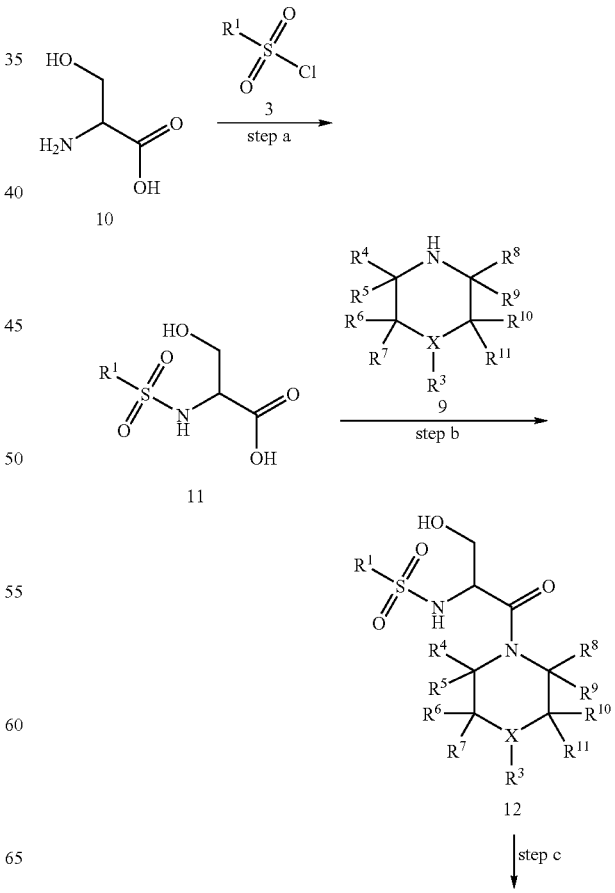

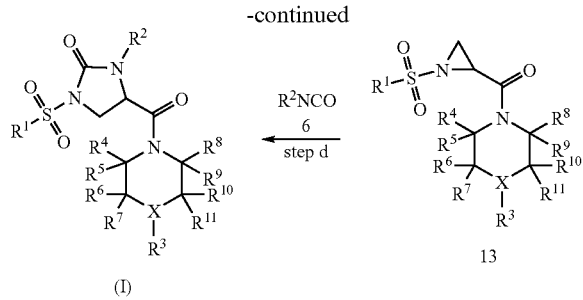

An alternative synthesis of compounds of formula (I) is described in scheme 2: Sulfonylation of serine 10, either in racemic or in enantiomerically pure form, can be achieved by treatment with a sulfonylchloride 3 in the presence of a base such as NaOH, Na₂CO₃ or NaHCO₃ in a solvent such as water, acetone, diethylether, tetrahydrofuran, toluene or mixtures thereof at a temperature between 0° C. and room temperature to give sulfonamide 11 (step a). Condensation of the carboxylic acid 11 and the amine 9 can be achieved by well known procedures for amide formation, such as the use of N-(3-dimethylaminopropyl)-N'-ethyl-carbodiimide-hydrochloride (EDCI), O-(1,2-dihydro-2-oxo-1-pyridyl)-N,N,N,N-tetra-methyluronium-tetrafluorborate (TPTU), O-(7-azabenzotriazol-1-yl)-1,1,3,3-tetramethyluronium hexafluorophosphate (HATU) or benzotriazol-1-yloxytris(dimethylamino)phosphonium hexafluorophoshate (BOP) or other coupling reagents in the presence of a base such as ethyl-diisopropyl-amine, triethylamine, N-methylmorpholine optionally in the presence of 4-dimethylamino-pyridine or 1-hydroxybenzo-triazole (HOBt) in solvents such as tetrahydrofuran, dichloromethane, dimethylformamide, dimethylacetamide or dioxane at temperatures between 0° C. and ambient temperature to give compound 12 (step b). Alternatively, a two-step procedure might be used: treatment of the acid 11 with oxalyl chloride in CH₂Cl₂ in the presence of DMF or with thionyl chloride in toluene, followed by reaction with the amine 9. Mitsunobu reaction of 12, that means treatment with a dialkylazodicarboxylate such as diethylazodicarboxylate, diisopropylazodicarboxylate or di-tert-butyldiazodicarboxylate and with triphenylphosphine in a solvent such as tetrahydrofuran at 0° C. to room temperature, leads to the formation of an aziridine 13 (step c). Alternatively, the hydroxy group of 12 can be converted into a leaving group by treatment with a sulfonylchloride such as methylsulfonyl chloride or tosyl chloride in the presence of a base such as N-ethyl-diisopropylamine, triethylamine or pyridine in a solvent such as dichloromethane or tetrahydrofuran at 0° C. to room temperature. Subsequent treatment with a base such as NaH, triethylamine or N-ethyl-diisopropylamine in a solvent such as tetrahydrofuran or N,N-dimethylacetamide at a temperature from 0° C. to reflux can give the aziridine 13. Treatment of 13 with an isocyanate 6 in the presence of a metal halide such as sodium iodide or magnesium bromide in a solvent such as tetrahydrofuran or dioxane at temperatures between 0° C. and room temperature gives compounds of formula (I) (step d).

Scheme 3: (Method C)

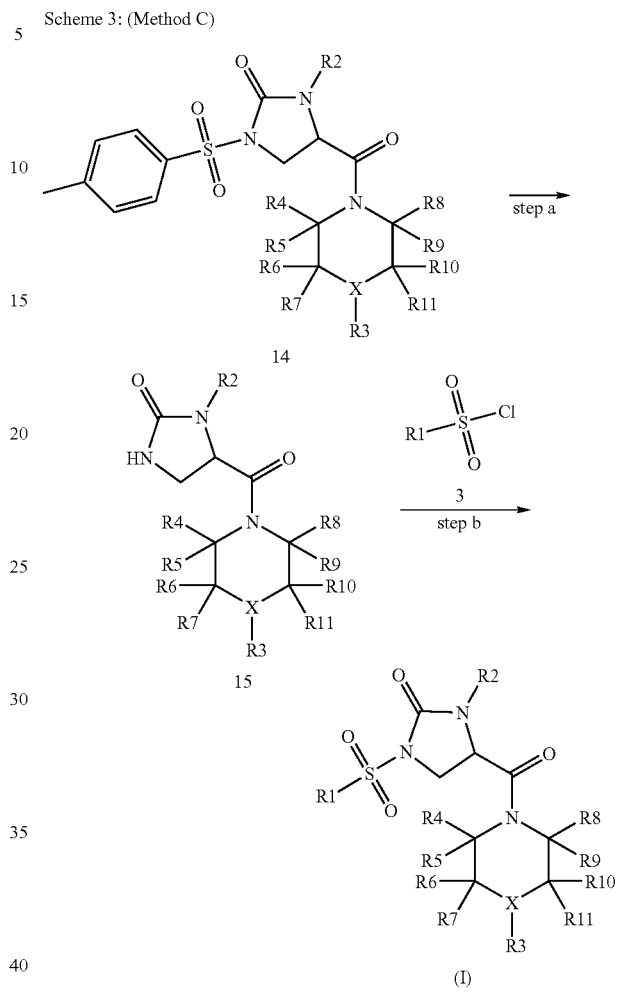

Another method to synthesize compounds of formula (I) is described in scheme 3: The N-arylsulfonyl bond of N-arylsulfonyl-imidazolidinones such as compounds 14 (obtained by method A or method B) can be cleaved under reducing conditions using magnesium in refluxing methanol (see *J. Heterocyclic Chem.* 2004, 41, 737) to give imidazolidinones 15 (step a). Sulfonylation of compounds 15 is achieved with sulfonyl chlorides 5 in solvents such dimethylacetamide, tetrahydrofuran, dioxane or dichloromethane in the presence of bases such as sodium hydride, N-ethyl-diisopropylamine or triethylamine optionally in the presence of DMAP at 0° C. to room temperature (step b).

Scheme 4 (Method D)

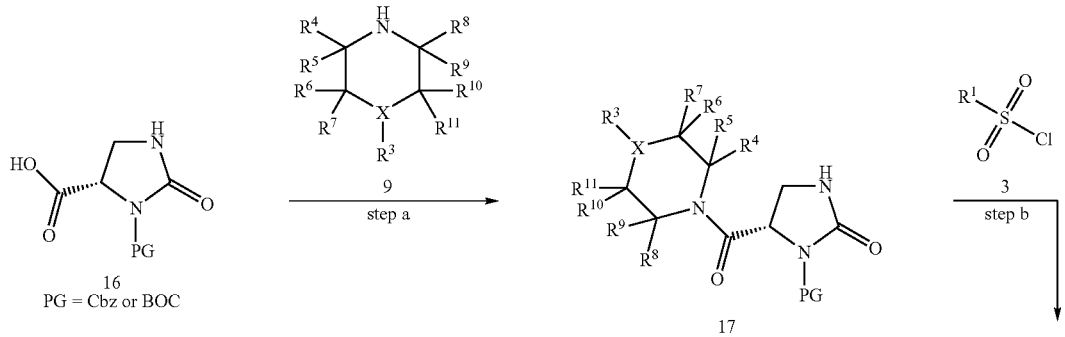

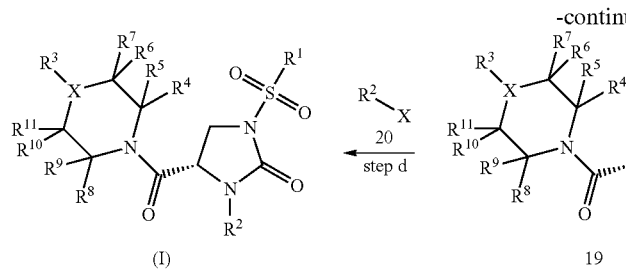 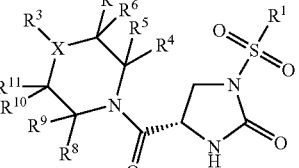 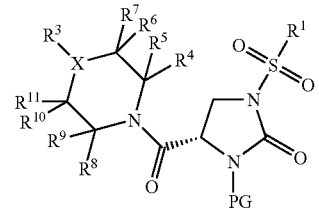

In scheme 4 an alternative synthesis of compounds of the general formula (I) is described. Appropriate protected (S)-(−)-oxo-1,5-imidazoline carboxylic acid 16 and amines 9 are either commercially available, described in the literature or can be prepared by methods well known to a person skilled in the art. Condensation of 16 and 9 can be achieved by well known procedures for amide formation, such as the use of N-(3-dimethylaminopropyl)-N'-ethyl-carbodiimide-hydrochloride (EDCI), O-(1,2-dihydro-2-oxo-1-pyridyl)-N,N,N,N-tetra-methyluronium-tetrafluorborate (TPTU), O-(7-azabenzotriazol-1-yl)-1,1,3,3-tetramethyluronium hexafluorophosphate (HATU) or benzotriazol-1-yloxytris (dimethylamino)phosphonium hexafluorophoshate (BOP) or other coupling reagents in the presence of a base such as ethyl-diisopropyl-amine, triethylamine, N-methylmorpholine optionally in the presence of 4-dimethylamino-pyridine or 1-hydroxybenzo-triazole (HOBt) in solvents such as dichloromethane, dimethylformamide, dimethylacetamide or dioxane at temperatures between 0° C. and ambient temperature (step a). Alternatively, a two-step procedure might be used: treatment of the acid 16 with oxalyl chloride in CH$_2$Cl$_2$ in the presence of DMF or with thionyl chloride in toluene, followed by reaction with the amine 9. Sulfonylation of compound 17 is achieved with sulfonyl chlorides 3 in solvents such as dichloromethane, THF, DMF or dioxane with bases such as N-ethyl-diisopropylamine or triethylamine optionally in the presence of DMAP at 0° C. to room temperature (step b). The protecting moiety (PG) of compounds 18 can be cleaved by hydrogenation in solvents as methanol, ethanol, ethyl acetate with Pd/C for Cbz-groups or using acidic conditions such as TFA in CH$_2$Cl$_2$ or HCl in dioxane for BOC-groups to yield sulfonyl urea 19 (step c). 19 may be treated with alkylating agents R$^2$—X 20 in which X is a leaving group such as Cl, Br, I, OMs, OTs, or OTf. These reactions are performed in the presence of a base such as Cs$_2$CO$_3$ or K$_2$CO$_3$ in inert solvents such as acetone, dioxane, DMF or DMA optionally in the presence of KI or NaI to give (I) (step d). Alternatively, sulfonyl urea 19 may be treated with alkylating agents R$^2$—X 20 in the presence of sodium hydride in solvents such as DMA, DMF or THF at temperatures between 0° C. to reflux of the solvent. For compounds of formula (I), in which R$^2$=aryl or heteroaryl, a palladium catalyzed arylation/heteroarylation of ureas may be used. Sulfonyl urea 19 may be treated with R$^2$—X 20 (with X=Cl, Br, I or TfO) using Xantphos, P(o-Tol)$_3$, or P(t-Bu)$_3$ as ligand, Pd(OAc)$_2$, Pd$_2$dba$_2$ as palladium source and bases such as NaOtBu, NaOH, Cs$_2$CO$_3$ in solvents such as dioxane, THF or toluene to yield (I).

The conversion of a compound of formula (I) into a pharmaceutically acceptable salt can be carried out by treatment of such a compound with an inorganic acid, for example a hydrohalic acid, such as, for example, hydrochloric acid or hydrobromic acid, or other inorganic acids such as sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. One method to form such a salt is e.g. by addition of 1/n equivalents of the acid, wherein n=number of acidic protons on the acid, to a solution of the compound in a suitable solvent (e.g. ethanol, ethanol-water mixture, tetrahydrofurane-water mixture) and to remove the solvent by evaporation or lyophilization.

Insofar as their preparation is not described in the examples, the compounds of formula (I) as well as all intermediate products can be prepared according to analogous methods or according to the methods set forth above. Starting materials are commercially available or known in the art.

As described above, the novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. They can therefore be used in the treatment and prophylaxis of diseases which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment of infectious diseases such as HIV as well as cancer and for prophylaxis of age-related and inherited (e.g. Stargardt's disease) forms of macular degeneration.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by LXR alpha and/or LXR beta agonists, particularly as therapeutically active substances for the treatment and/or prophylaxis of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease.

In another preferred embodiment, the invention relates to a method for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease, which method comprises administering a compound as defined above to a human being or animal.

The invention also embraces the use of compounds as defined above for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease.

The invention also relates to the use of compounds as described above for the preparation of pharmaceutical compositions for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease. Such pharmaceutical compositions comprise a compound as described above.

Prevention and/or treatment of increased lipid levels, increased cholesterol levels, atherosclerotic diseases, dyslipidemia, or diabetes is the preferred indication, particularly prevention and/or treatment of increased lipid levels, increased cholesterol levels, atherosclerotic diseases, or dyslipidemia, especially prevention and/or treatment of atherosclerotic diseases or dyslipidemia. Diabetes, particularly non-insulin dependent diabetes mellitus, is another preferred disease.

The following tests were carried out in order to determine the activity of the compounds of the present invention. Background information on the performed assays can be found in: Nichols J S et al. "Development of a scintillation proximity assay for peroxisome proliferator-activated receptor gamma ligand binding domain", Anal Biochem. 1998, 257: 112-119.

Mammalian expression vectors were constructed to express full-length human LXR alpha and LXR beta. Bacterial expression vectors were constructed to produce tagged versions of the ligand binding domains (LBD) of human LXR alpha (aa 164 to 447) and human LXR beta (aa 155 to 460). To accomplish this, the portions of the sequences encoding the LBDs were amplified from the full-length clones by PCR and then subcloned into the plasmid vectors. Final clones were verified by DNA sequence analysis (Willy et al., Genes Dev. 1995, 9:1033-45; Song et al., Proc Natl Acad Sci USA.1994, 91:10809-13).

Induction, expression, and purification of LBD proteins were performed in $E.\ coli$ strain BL21 (pLysS) cells by standard methods (Ref: Current Protocols in Molecular Biology, Wiley Press, edited by Ausubel et al).

Radioligand Binding Assay

LXR alpha and LXR beta receptor binding were assayed in buffer consisting of 50 mM HEPES, pH 7.4, 10 mM NaCl, 5 mM $MgCl_2$. For each 96-well reaction, 500 ng of LXRα-LBD or 700 ng of LXR beta-LBD proteins were bound to 80 µg or 40 µg SPA beads respectively, in a final volume of 50 µl by shaking. The resulting slurry was incubated for 1 h at RT and centrifuged for 2 min at 1300×g. The supernatant containing unbound protein was removed, and the semi-dry pellet containing the receptor-coated beads was re-suspended in 50 µl of buffer. Radioligand (eg. 100,000 dpm of (N-(2,2,2-trifluoroethyl)-N-[4-(2,2,2-trifluoro-1-hydroxy-1-trifluoromethylethyl)-phenyl]-benzenesulfonamide)) was added, and the reaction incubated at RT for 1 h in the presence of test compounds, and then scintillation proximity counting was performed. All binding assays were performed in 96-well plates and the amount of bound ligand was measured on a Packard TopCount using OptiPlates (Packard). Dose response curves were measured within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95%02:5% $CO_2$ atmosphere. Cells were seeded in 6-well plates at a density of $10^5$ Cells/well and then batch-transfected with either the full-length-LXRα or full-length-LXRβ expression plasmids plus a reporter plasmid expressing luciferase under the control of LXR response elements. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 µl of phenol red-free medium containing the test substances or control ligands (final DMSO concentration: 0.1%). Following incubation of the cells for 24 hours with substances, 50 µl of the supernatant was discarded and then 50 µl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays (EC50 or IC50) of 1 nM to 100 µM, preferably 1 nM to 10 µM, more preferably 1 nM to 1 µM.

For example, the following compounds showed the following $IC_{50}$ values in the binding assay:

| Example | LXRalpha Binding $IC_{50}$ [µmol/l] | LXRbeta Binding $IC_{50}$ [µmol/l] |
| --- | --- | --- |
| 39 | 5.5 | 0.48 |
| 50 | 0.26 | 0.10 |
| 63 | 2.5 | 0.24 |

These results have been obtained by using the foregoing test.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following Examples serve to illustrate the present invention in more detail. They are, however, not intended to limit its scope in any manner. MS=mass spectrometry.

EXAMPLES

Example 1

(RS)-4-[4-(2,5-Dimethyl-phenyl)-piperazine-1-carbonyl]-1-(3-methoxy-benzenesulfonyl)-3-phenyl-imidazolidin-2-one Step 1: To a suspension of DL-serinemethylester hydrochloride (0.481 g) in dichloromethane (5 ml) was added 3-methoxybenzene sulfonylchloride (0.639 g). N-Ethyl-di-isopropylamine (0.839 g) was added and the mixture was stirred at room temperature for 16 h. The reaction mixture was washed with water. The organic phase was dried ($MgSO_4$), filtered and evaporated to dryness. The crude product was used in the next step without further purification.

Step 2: The crude product of step 1 was dissolved in tetrahydrofuran (5 ml). The solution was cooled to 0° C. under an argon atmosphere. Triphenylphosphine (0.896 g) and diethylazodicarboxylate (DEAD, 0.595 g) were added. The mixture was stirred for 1 day at room temperature. The solvent was evaporated. The product was purified by chromatography ($SiO_2$, cyclohexane/ethyl acetate 4:1=>1:4) to give (RS)-1-(3-methoxy-benzenesulfonyl)-aziridine-2-carboxylic acid methyl ester (0.496 g) as a colorless oil.

Step 3: To a solution of (RS)-1-(3-methoxy-benzenesulfonyl)-aziridine-2-carboxylic acid methyl ester (0.098 g) in tetrahydrofuran (3 ml) were added sodium iodide (0.054 g) and phenylisocyanate (0.043 g). The mixture was stirred for 18 h at room temperature. The mixture was diluted with ethyl acetate and washed with water, 1% aqueous $Na_2S_2O_3$ solution and again with water. The organic phase was dried, filtered and evaporated. The product was purified by chromatography ($SiO_2$, cyclohexane/ethyl acetate 9:1=>1:1) to give (RS)-1-(3-methoxy-benzenesulfonyl)-2-oxo-3-phenyl-imidazolidine-4-carboxylic acid methyl ester (0.060 g) as a colorless solid. MS: 391.1 ($[M+H]^+$)

Step 4: To a solution of (RS)-1-(3-methoxy-benzenesulfonyl)-2-oxo-3-phenyl-imidazolidine-4-carboxylic acid methyl ester (0.043 g) in tetrahydrofuran (0.5 ml) and methanol (0.5 ml) was added a 1 M aqueous NaOH solution (0.13 ml) at 0° C. The mixture was stirred at 0° C. for 30 min. 1 M HCl (0.15 ml) was added and the organic solvents were evaporated. The colorless precipitate was collected by filtration, washed with water and dried to give (RS)-1-(3-methoxy-benzenesulfonyl)-2-oxo-3-phenyl-imidazolidine-4-carboxylic acid (0.040 g) as a colorless solid.

Step 5: To a solution of (RS)-1-(3-methoxy-benzenesulfonyl)-2-oxo-3-phenyl-imidazolidine-4-carboxylic acid (0.040 g) in tetrahydrofuran (2 ml) were added 1-(2,5-dimethylphenyl)-piperazine (0.030 g), (benzotriazol-1-yloxy)-tris-(dimethylamino)-phosphonium-hexafluorophosphate (BOP reagent, 0.071 g) and N-ethyl-diisopropylamine (0.041 g). The mixture was stirred at room temperature for 4 h. The solvent was evaporated and the product was purified by chromatography ($SiO_2$, cyclohexane/ethyl acetate 4:1=>1:1) to give (RS)-4-[4-(2,5-dimethyl-phenyl)-piperazine-1-carbonyl]-1-(3-methoxy-benzenesulfonyl)-3-phenyl-imidazolidin-2-one (0.065 g) as a colorless solid. MS: 549.0 ($[M+H]^+$)

Example 2

(RS)-1-Benzenesulfonyl-4-[4-(2,5-dimethyl-phenyl)-piperazine-1-carbonyl]-3-phenyl-imidazolidin-2-one Step 1: DL-serine (1.051 g) was dissolved in a 1 M aqueous NaOH solution (20 ml). Benzenesulfonyl chloride (1.77 g) was added at 0° C. After 30 min the ice bath was removed and the mixture was stirred for 18 h at room temperature. The mixture was again placed in an ice bath. The mixture was acidified to pH 1 using 25% aqueous HCl. The colorless precipitate was collected by filtration, washed with 1 M HCl and dried to give (RS)-2-benzenesulfonylamino-3-hydroxy-propionic acid (1.23 g) as a colorless solid.

Step 2: (RS)-2-benzenesulfonylamino-3-hydroxy-propionic acid (1.204 g) was dissolved in tetrahydrofuran (15 ml) and cooled to 0° C. 1-(2,5-Dimethylphenyl)-piperazine (1.12 g), (benzotriazol-1-yloxy)-tris-(dimethylamino)-phosphonium-hexafluorophosphate (BOP reagent, 3.26 g) and N-ethyl-diisopropylamine (1.90 g) were added. The mixture was stirred at room temperature for 18 h. Ethyl acetate and a 10% KHSO$_4$ solution were added. The organic phase was washed with water, dried, filtered and evaporated. The product was purified by chromatography (SiO$_2$, cyclohexane/ethyl acetate 1:1=>ethyl acetate) to give (RS)—N-{2-[4-(2,5-dimethyl-phenyl)-piperazin-1-yl]-1-hydroxymethyl-2-oxo-ethyl}-benzenesulfonamide (1.45 g) as a colorless foam. MS: 418.3 ([M+H]$^+$)

Step 3: To a solution of (RS)—N-{2-[4-(2,5-dimethyl-phenyl)-piperazin-1-yl]-1-hydroxymethyl-2-oxo-ethyl}-benzenesulfonamide (1.417 g) and triphenylphosphine (0.979 g) in tetrahydrofuran (12 ml) was added diethylazodicarboxylate (DEAD, 0.65 g) at 0° C. After 15 min the ice bath was removed and the mixture was stirred at room temperature for 45 min. The solvent was evaporated and the product was purified by chromatography (SiO$_2$, cyclohexane/ethyl acetate 4:1=>1:1) to give (RS)-(1-benzenesulfonyl-aziridin-2-yl)-[4-(2,5-dimethyl-phenyl)-piperazin-1-yl]-methanone (0.934 g) as a colorless solid.

Step 4: To a solution of (RS)-(1-benzenesulfonyl-aziridin-2-yl)-[4-(2,5-dimethyl-phenyl)-piperazin-1-yl]-methanone (0.084 g) in tetrahydrofuran (2 ml) were added sodium iodide (0.035 g) and phenylisocyanate (0.038 g). The mixture was stirred for 3 h at room temperature. The mixture was diluted with ethyl acetate and washed with water, 1% aqueous Na$_2$S$_2$O$_3$ solution and again with water. The organic phase was dried, filtered and evaporated. The product was purified by chromatography (SiO$_2$, cyclohexane/ethyl acetate 4:1=>1:1) to give (RS)-1-benzenesulfonyl-4-[4-(2,5-dimethyl-phenyl)-piperazine-1-carbonyl]-3-phenyl-imidazolidin-2-one (0.071 g) as a colorless solid. MS: 519.3 ([M+H]$^+$)

Example 3

(RS)-1-(3-Methoxy-benzenesulfonyl)-4-[4-(2-methoxy-phenyl)-piperazine-1-carbonyl]-3-phenyl-imidazolidin-2-one In analogy to example 1, (RS)-1-(3-methoxy-benzenesulfonyl)-2-oxo-3-phenyl-imidazolidine-4-carboxylic acid (step 4 of example 1) was reacted with 1-(2-methoxyphenyl)-piperazine to give the title compound as a colorless solid. MS: 551.3 ([M+H]$^+$)

Example 4

(RS)-1-(3-Methoxy-benzenesulfonyl)-3-phenyl-4-[4-(3-trifluoromethyl-phenyl)-piperazine-1-carbonyl]-imidazolidin-2-one In analogy to example 1, (RS)-1-(3-methoxy-benzenesulfonyl)-2-oxo-3-phenyl-imidazolidine-4-carboxylic acid (step 4 of example 1) was reacted with N-(3-trifluoromethylphenyl)-piperazine to give the title compound as a colorless solid. MS: 588.5 ([M+H]$^+$)

Example 5

(RS)-1-(3-Methoxy-benzenesulfonyl)-3-phenyl-4-[4-(3-trifluoromethyl-pyridin-2-yl)-piperazine-1-carbonyl]-imidazolidin-2-one In analogy to example 1, (RS)-1-(3-methoxy-benzenesulfonyl)-2-oxo-3-phenyl-imidazolidine-4-carboxylic acid (step 4 of example 1) was reacted with 1-[3-(trifluoromethyl)pyrid-2-yl]-piperazine to give the title compound as a colorless solid. MS: 589.8 ([M+H]$^+$)

Example 6

(RS)-1-(3-Methoxy-benzenesulfonyl)-4-[4-(3-methyl-pyridin-2-yl)-piperazine-1-carbonyl]-3-phenyl-imidazolidin-2-one In analogy to example 1, (RS)-1-(3-methoxy-benzenesulfonyl)-2-oxo-3-phenyl-imidazolidine-4-carboxylic acid (step 4 of example 1) was reacted with 1-(3-methyl-pyridin-2-yl)piperazine to give the title compound as a colorless solid. MS: 536.2 ([M+H]$^+$)

Example 7

(RS)-1-(3-Methoxy-benzenesulfonyl)-4-[4-(2-methoxy-phenyl)-piperidine-1-carbonyl]-3-phenyl-imidazolidin-2-one In analogy to example 1, (RS)-1-(3-methoxy-benzenesulfonyl)-2-oxo-3-phenyl-imidazolidine-4-carboxylic acid (step 4 of example 1) was reacted with 4-(2-methoxyphenyl)piperidine to give the title compound as a colorless solid. MS: 550.0 ([M+H]t)

Example 8

(RS)-3-(2-Chloro-phenyl)-4-[4-(2,5-dimethyl-phenyl)-piperazine-1-carbonyl]-1-(3-methoxy-benzenesulfonyl)-imidazolidin-2-one In analogy to example 1, (RS)-1-(3-methoxy-benzenesulfonyl)-aziridine-2-carboxylic acid methyl ester (step 2 of example 1) was first reacted with sodium iodide and 2-chlorophenylisocyanate; subsequent ester hydrolysis using sodium hydroxide and coupling with 1-(2,5-dimethylphenyl)-piperazine gave the title compound as a colorless solid. MS: 583.3 ([M+H]$^+$)

Example 9

(RS)-4-[4-(5-Chloro-2-methyl-phenyl)-piperazine-1-carbonyl]-3-(2-chloro-phenyl)-1-(3-methoxy-benzenesulfonyl)-imidazolidin-2-one In analogy to example 1, (RS)-1-(3-methoxy-benzenesulfonyl)-aziridine-2-carboxylic acid methyl ester (step 2 of example 1) was first reacted with sodium iodide and 2-chlorophenylisocyanate; subsequent ester hydrolysis using sodium hydroxide and coupling with 1-(5-chloro-2-methylphenyl)-piperazine gave the title compound as a colorless solid. MS: 603.3 ([M+H]$^+$)

Example 10

(RS)-4-[4-(2,5-Dimethyl-phenyl)-piperazine-1-carbonyl]-3-phenyl-1-(toluene-4-sulfonyl)-imidazolidin-2-one Step 1: In analogy to example 2, DL-serine was reacted with 4-toluenesulfonyl chloride to give 3-hydroxy-2-(toluene-4-sulfonylamino)-propionic acid.

Step 2: In analogy to example 2,3-hydroxy-2-(toluene-4-sulfonylamino)-propionic acid was reacted with 1-(2,5-dimethylphenyl)-piperazine to give N-{2-[4-(2,5-dimethyl-phenyl)-piperazin-1-yl]-1-hydroxymethyl-2-oxo-ethyl}-4-methyl-benzenesulfonamide.

Step 3: In analogy to example 2, N-{2-[4-(2,5-dimethyl-phenyl)-piperazin-1-yl]-1-hydroxymethyl-2-oxo-ethyl}-4-methyl-benzenesulfonamide was reacted with triphenylphosphine and diethylazodicarboxylate to give [4-(2,5-dimethyl-phenyl)-piperazin-1-yl]-[1-(toluene-4-sulfonyl)-aziridin-2-yl]-methanone.

Step 4: In analogy to example 2, [4-(2,5-dimethyl-phenyl)-piperazin-1-yl]-[1-(toluene-4-sulfonyl)-aziridin-2-yl]-methanone was reacted with sodium iodide and phenylisocyanate to give the title compound as a colorless solid. MS: 532.8 ([M+H]$^+$)

Example 11

(RS)-4-[4-(2,5-Dimethyl-phenyl)-piperazine-1-carbonyl]-3-phenyl-1-(2-trifluoromethyl-benzenesulfonyl)-imidazolidin-2-one Steps 1 and 2: In analogy to example 1, DL-serinemethylester hydrochloride was reacted with 2-trifluoromethylbenzenesulphonylchloride. Subsequent treatment with triphenylphosphine and diethylazodicarboxylate gave (RS)-1-(2-trifluoromethyl-benzenesulfonyl)-aziridine-2-carboxylic acid methyl ester.

Step 3: In analogy to example 1, (RS)-1-(2-trifluoromethyl-benzenesulfonyl)-aziridine-2-carboxylic acid methyl ester was reacted with phenylisocyanate and sodiumiodide to give (RS)-2-oxo-3-phenyl-1-(2-trifluoromethyl-benzenesulfonyl)-imidazolidine-4-carboxylic acid methyl ester.

Steps 4 and 5: In analogy to example 1, (RS)-2-oxo-3-phenyl-1-(2-trifluoromethyl-benzenesulfonyl)-imidazolidine-4-carboxylic acid methyl ester was hydrolyzed using sodium hydroxide solution to give (RS)-2-oxo-3-phenyl-1-(2-trifluoromethyl-benzenesulfonyl)-imidazolidine-4-carboxylic acid. Finally, (RS)-2-oxo-3-phenyl-1-(2-trifluoromethyl-benzenesulfonyl)-imidazolidine-4-carboxylic acid was coupled with 1-(2,5-dimethylphenyl)piperazine to give the title compound as a colorless solid. MS: 586.8 ([M+H]$^+$)

Example 12

(RS)-4-[4-(5-Chloro-2-methyl-phenyl)-piperazine-1-carbonyl]-3-phenyl-1-(2-trifluoromethyl-benzenesulfonyl)-imidazolidin-2-one In analogy to example 1, (RS)-2-oxo-3-phenyl-1-(2-trifluoromethyl-benzenesulfonyl)-imidazolidine-4-carboxylic acid (example 11, step 4) was coupled with 1-(5-chloro-ortho-tolyl)-piperazine to give the title compound as a colorless solid. MS: 608.5 ([M+H]$^+$)

Example 13

(RS)-2-{4-[2-Oxo-3-phenyl-1-(2-trifluoromethyl-benzenesulfonyl)-imidazolidine-4-carbonyl]-piperazin-1-yl}-benzonitrile In analogy to example 1, (RS)-2-oxo-3-phenyl-1-(2-trifluoromethyl-benzenesulfonyl)-imidazolidine-4-carboxylic acid (example 11, step 4) was coupled with 1-(2-cyanophenyl)-piperazine to give the title compound as a colorless solid. MS: 583.5 ([M+H]$^+$)

Example 14

(RS)-1-Benzenesulfonyl-4-[4-(2,5-dimethyl-phenyl)-piperazine-1-carbonyl]-3-ethyl-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and ethyl isocyanate to give the title compound as a colorless solid. MS: 471.1 ([M+H]$^+$)

Example 15

(RS)-1-Benzenesulfonyl-4-[4-(2,5-dimethyl-phenyl)-piperazine-1-carbonyl]-3-isopropyl-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and isopropyl isocyanate to give the title compound as a colorless solid. MS: 485.2 ([M+H]$^+$)

Example 16

(RS)-1-Benzenesulfonyl-4-[4-(2,5-dimethyl-phenyl)-piperazine-1-carbonyl]-3-propyl-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and propyl isocyanate to give the title compound as a colorless solid. MS: 485.2 ([M+H]$^+$)

Example 17

(RS)-3-Allyl-1-benzenesulfonyl-4-[4-(2,5-dimethyl-phenyl)-piperazine-1-carbonyl]-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and allyl isocyanate to give the title compound as a colorless solid. MS: 483.2 ([M+H]$^+$)

Example 18

(RS)-1-Benzenesulfonyl-3-butyl-4-[4-(2,5-dimethyl-phenyl)-piperazine-1-carbonyl]-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and butyl isocyanate to give the title compound as a colorless solid. MS: 499.0 ([M+H]$^+$)

Example 19

(RS)-1-Benzenesulfonyl-3-cyclopentyl-4-[4-(2,5-dimethyl-phenyl)-piperazine-1-carbonyl]-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and cyclopentyl isocyanate to give the title compound as a colorless solid. MS: 511.1 ([M+H]$^+$)

Example 20

(RS)-1-Benzenesulfonyl-3-cyclohexyl-4-[4-(2,5-dimethyl-phenyl)-piperazine-1-carbonyl]-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and cyclohexyl isocyanate to give the title compound as a colorless solid. MS: 525.4 ([M+H]$^+$)

Example 21

(S)-1-Benzenesulfonyl-4-[4-(2,5-dimethyl-phenyl)-piperazine-1-carbonyl]-3-phenyl-imidazolidin-2-one Step 1: In analogy to example 2, L-serine was reacted with benzenesulfonyl chloride to give (S)-2-benzenesulfonylamino-3-hydroxy-propionic acid.

Step 2: In analogy to example 2, (S)-2-benzenesulfonylamino-3-hydroxy-propionic acid was coupled with 1-(2,5-dimethylphenyl)-piperazine to give N-{(S)-2-[4-(2,5-dimethyl-phenyl)-piperazin-1-yl]-1-hydroxymethyl-2-oxo-ethyl}-benzenesulfonamide.

Step 3: In analogy to example 2, N-{(S)-2-[4-(2,5-dimethyl-phenyl)-piperazin-1-yl]-1-hydroxymethyl-2-oxo-ethyl}-benzenesulfonamide was reacted with triphenylphosphine and diethylazodicarboxylate to give ((S)-1-benzenesulfonyl-aziridin-2-yl)-[4-(2,5-dimethyl-phenyl)-piperazin-1-yl]-methanone.

Step 4: In analogy to example 2, ((S)-1-benzenesulfonyl-aziridin-2-yl)-[4-(2,5-dimethyl-phenyl)-piperazin-1-yl]-methanone was reacted with sodium iodide and phenylisocyanate to give the title compound as a colorless solid. MS: 519.3 ([M+H]$^+$)

Example 22

(R)-1-Benzenesulfonyl-4-[4-(2,5-dimethyl-phenyl)-piperazine-1-carbonyl]-3-phenyl-imidazolidin-2-one Step 1: In analogy to example 2, D-serine was reacted with benzenesulfonyl chloride to give (R)-2-benzenesulfonylamino-3-hydroxy-propionic acid.

Step 2: In analogy to example 2, (R)-2-benzenesulfonylamino-3-hydroxy-propionic acid was coupled with 1-(2,5-dimethylphenyl)-piperazine to give N-{(R)-2-[4-(2,5-dimethyl-phenyl)-piperazin-1-yl]-1-hydroxymethyl-2-oxo-ethyl}-benzenesulfonamide.

Step 3: In analogy to example 2, N-{(R)-2-[4-(2,5-dimethyl-phenyl)-piperazin-1-yl]-1-hydroxymethyl-2-oxo-ethyl}-benzenesulfonamide was reacted with triphenylphosphine and diethylazodicarboxylate to give ((R)-1-benzenesulfonyl-aziridin-2-yl)-[4-(2,5-dimethyl-phenyl)-piperazin-1-yl]-methanone.

Step 4: In analogy to example 2, ((R)-1-benzenesulfonyl-aziridin-2-yl)-[4-(2,5-dimethyl-phenyl)-piperazin-1-yl]-methanone was reacted with sodium iodide and phenylisocyanate to give the title compound as a colorless solid. MS: 519.0 ([M+H]$^+$)

Example 23

(S)-1-Benzenesulfonyl-4-[4-(2,5-dimethyl-phenyl)-piperazine-1-carbonyl]-3-(2-fluoro-phenyl)-imidazolidin-2-one In analogy to example 2, ((S)-1-benzenesulfonyl-aziridin-2-yl)-[4-(2,5-dimethyl-phenyl)-piperazin-1-yl]-methanone (example 21, step 3) was reacted with sodium iodide and 2-fluorophenylisocyanate to give the title compound as a colorless solid. MS: 537.0 ([M+H]$^+$)

Example 24

(RS)-1-Benzenesulfonyl-3-(2-chloro-phenyl)-4-[4-(2,5-dimethyl-phenyl)-piperazine-1-carbonyl]-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and 2-chlorophenyl isocyanate to give the title compound as a colorless solid. MS: 553.3 ([M+H]$^+$)

Example 25

(RS)-1-Benzenesulfonyl-3-(3-chloro-phenyl)-4-[4-(2,5-dimethyl-phenyl)-piperazine-1-carbonyl]-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and 3-chlorophenyl isocyanate to give the title compound as a colorless solid. MS: 552.7 ([M+H]$^+$)

Example 26

(RS)-1-Benzenesulfonyl-3-(4-chloro-phenyl)-4-[4-(2,5-dimethyl-phenyl)-piperazine-1-carbonyl]-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and 4-chlorophenyl isocyanate to give the title compound as a colorless solid. MS: 552.7 ([M+H]$^+$)

Example 27

(RS)-1-Benzenesulfonyl-4-[4-(2,5-dimethyl-phenyl)-piperazine-1-carbonyl]-3-(4-fluoro-phenyl)-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and 4-fluorophenyl isocyanate to give the title compound as a colorless solid. MS: 537.0 ([M+H]$^+$)

Example 28

(S)-1-Benzenesulfonyl-4-[4-(2,5-dimethyl-phenyl)-piperazine-1-carbonyl]-3-(4-fluoro-phenyl)-imidazolidin-2-one In analogy to example 2, ((S)-1-benzenesulfonyl-aziridin-2-yl)-[4-(2,5-dimethyl-phenyl)-piperazin-1-yl]-methanone (example 21, step 3) was reacted with sodium iodide and 4-fluorophenylisocyanate to give the title compound as a colorless solid. MS: 537.2 ([M+H]$^+$)

Example 29

(S)-1-Benzenesulfonyl-3-(2,4-difluoro-phenyl)-4-[4-(2,5-dimethyl-phenyl)-piperazine-1-carbonyl]-imidazolidin-2-one In analogy to example 2, ((S)-1-benzenesulfonyl-aziridin-2-yl)-[4-(2,5-dimethyl-phenyl)-piperazin-1-yl]-methanone (example 21, step 3) was reacted with sodium iodide and 2,4-difluorophenylisocyanate to give the title compound as a colorless solid. MS: 554.8 ([M+H]+)

Example 30

(RS)-1-Benzenesulfonyl-3-benzyl-4-[4-(2,5-dimethyl-phenyl)-piperazine-1-carbonyl]-imidazolidin-2-one In analogy to example 2, (RS)-(1-benzenesulfonyl-aziridin-2-yl)-[4-(2,5-dimethyl-phenyl)-piperazin-1-yl]-methanone (example 2, step 3) was reacted with sodium iodide and benzyl isocyanate to give the title compound as a colorless solid. MS: 532.9 ([M+H]$^+$)

Example 31

(+)-4-[4-(5-Chloro-2-methyl-phenyl)-piperazine-1-carbonyl]-3-(2-chloro-phenyl)-1-(3-methoxy-benzenesulfonyl)-imidazolidin-2-one and

Example 32

(−)-4-[4-(5-Chloro-2-methyl-phenyl)-piperazine-1-carbonyl]-3-(2-chloro-phenyl)-1-(3-methoxy-benzenesulfonyl)-imidazolidin-2-one (RS)-4-[4-(5-Chloro-2-methyl-phenyl)-piperazine-1-carbonyl]-3-(2-chloro-phenyl)-1-(3-methoxy-benzenesulfonyl)-imidazolidin-2-one (example 9) was separated into the enantiomers by chiral HPLC on Chiralpak AD using heptane/30% isopropanol as the mobile phase to give (+)-4-[4-(5-chloro-2-methyl-phenyl)-piperazine-1-carbonyl]-3-(2-chloro-phenyl)-1-(3-methoxy-benzenesulfonyl)-imidazolidin-2-one (MS: 604.7 [M+H]$^+$) and (−)-4-[4-(5-chloro-2-methyl-phenyl)-piperazine-1-carbonyl]-3-(2-chloro-phenyl)-1-(3-methoxy-benzenesulfonyl)-imidazolidin-2-one (MS: 604.7 [M+H]$^+$) as colorless solids.

Example 33

(RS)-1-(3-Chloro-benzenesulfonyl)-4-[4-(2,5-dimethyl-phenyl)-piperazine-1-carbonyl]-3-phenyl-imidazolidin-2-one Step 1: A suspension of (RS)-4-[4-(2,5-dimethyl-phenyl)-piperazine-1-carbonyl]-3-phenyl-1-(toluene-4-sulfonyl)-imidazolidin-2-one (example 10, 0.59 g) and magnesium powder (0.215 g) in methanol (25 ml) was refluxed for 7 h and stirred at room temperature for 18 h. The mixture was filtered and the filtrate was concentrated. The product was purified by chromatography ((SiO$_2$, ethyl acetate=>ethyl acetate/methanol 95:5) to give (RS)-5-[4-(2,5-dimethyl-phenyl)-piperazine-1-carbonyl]-1-phenyl-imidazolidin-2-one (0.292 g) as a colorless solid.

Step 2: To a solution of (RS)-5-[4-(2,5-dimethyl-phenyl)-piperazine-1-carbonyl]-1-phenyl-imidazolidin-2-one (0.050 g) in dimethylacetamide (1 ml) under an argon atmosphere was added sodium hydride (55% in mineral oil, 6.3 mg) at 0° C. The mixture was stirred at 0° C. for 30 min. 3-Chlorobenzenesulfonyl chloride was added. The mixture was stirred at 0° C. for 30 min and at room temperature for 2 h. Water was added and the mixture was extracted with ethyl acetate. The organic phase was washed with water and concentrated. The product was purified by chromatography ((SiO$_2$, cyclohexane=>cyclohexane/ethyl acetate 1:2) to give (RS)-1-(3-chloro-benzenesulfonyl)-4-[4-(2,5-dimethyl-phenyl)-piperazine-1-carbonyl]-3-phenyl-imidazolidin-2-one (0.049 g) as a colorless solid. MS: 552.7 ([M+H]$^+$)

Example 34

(RS)-1-(2-Chloro-benzenesulfonyl)-4-[4-(2,5-dimethyl-phenyl)-piperazine-1-carbonyl]-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 2-chlorobenzenesulfonyl chloride to give the title compound as a colorless solid. MS: 552.7 ([M+H]$^+$)

Example 35

(RS)-1-(2,4-Difluoro-benzenesulfonyl)-4-[4-(2,5-dimethyl-phenyl)-piperazine-1-carbonyl]-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 2,4-difluorobenzenesulfonyl chloride to give the title compound as a colorless solid. MS: 555.2 ([M+H]$^+$)

Example 36

(RS)-4-[4-(2,5-Dimethyl-phenyl)-piperazine-1-carbonyl]-3-phenyl-1-(3,3,3-trifluoro-propane-1-sulfonyl)-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 3,3,3-trifluoropropane-1-sulfonyl chloride to give the title compound as an off-white solid. MS: 539.0 ([M+H]$^+$)

Example 37

(RS)-4-[4-(2,5-Dimethyl-phenyl)-piperazine-1-carbonyl]-3-phenyl-1-(propane-2-sulfonyl)-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and isopropylsulfonyl chloride to give the title compound as an off-white solid. MS: 485.2 ([M+H]$^+$)

Example 38

(RS)-1-(Butane-1-sulfonyl)-4-[4-(2,5-dimethyl-phenyl)-piperazine-1-carbonyl]-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 1-butanesulfonyl chloride to give the title compound as an off-white solid. MS: 499.0 ([M+H]$^+$)

Example 39

(RS)-1-Benzenesulfonyl-3-cyclohexyl-4-[4-(3-trifluoromethyl-pyridin-2-yl)-piperazine-1-carbonyl]-imidazolidin-2-one Step 1: In analogy to example 1, DL-serinemethylester hydrochloride was reacted with benzenesulfonyl chloride to give 2-benzenesulfonylamino-3-hydroxy-propionic acid methyl ester.

Step 2: In analogy to example 1,2-benzenesulfonylamino-3-hydroxy-propionic acid methyl ester was treated with triphenylphosphine and DEAD to give 1-benzenesulfonyl-aziridine-2-carboxylic acid methyl ester.

Step 3: In analogy to example 1,1-benzenesulfonyl-aziridine-2-carboxylic acid methyl ester was reacted with NaI and cyclohexylisocyanate to give 1-benzenesulfonyl-3-cyclohexyl-2-oxo-imidazolidine-4-carboxylic acid methyl ester.

Step 4: In analogy to example 1,1-benzenesulfonyl-3-cyclohexyl-2-oxo-imidazolidine-4-carboxylic acid methyl ester was hydrolyzed with NaOH solution to give (RS)-1-benzenesulfonyl-3-cyclohexyl-2-oxo-imidazolidine-4-carboxylic acid.

Step 5: In analogy to example 1, (RS)-1-benzenesulfonyl-3-cyclohexyl-2-oxo-imidazolidine-4-carboxylic acid was coupled with 1-[3-(trifluoromethyl)pyrid-2-yl]piperazine to give the title compound as a colorless solid. MS: 565.8 ([M+H]$^+$)

Example 40

(RS)-1-Benzenesulfonyl-4-[4-(3-chloro-5-trifluoromethyl-pyridin-2-yl)-piperazine-1-carbonyl]-3-cyclohexyl-imidazolidin-2-one In analogy to example 1, (RS)-1-benzenesulfonyl-3-cyclohexyl-2-oxo-imidazolidine-4-carboxylic acid (example 39, step 4) was coupled with 1-[3-chloro-5-(trifluoromethyl)pyrid-2-yl]piperazine to give the title compound as an off-white solid. MS: 600.3 ([M+H]$^+$)

Example 41

(RS)-2-[4-(1-Benzenesulfonyl-3-cyclohexyl-2-oxo-imidazolidine-4-carbonyl)-piperazin-1-yl]-nicotinonitrile In analogy to example 1, (RS)-1-benzenesulfonyl-3-cyclohexyl-2-oxo-imidazolidine-4-carboxylic acid (example 39, step 4) was coupled with 1-(2-(3-cyanopyridyl))piperazine to give the title compound as a colorless solid. MS: 523.3 ([M+H]$^+$)

Example 42

(RS)-1-Benzenesulfonyl-3-cyclohexyl-4-(4-pyridin-2-yl-piperazine-1-carbonyl)-imidazolidin-2-one In analogy to example 1, (RS)-1-benzenesulfonyl-3-cyclohexyl-2-oxo-imidazolidine-4-carboxylic acid (example 39, step 4) was coupled with 1-(2-pyridyl)piperazine to give the title compound as an off-white solid. MS: 498.3 ([M+H]$^+$)

Example 43

(RS)-1-Benzenesulfonyl-3-cyclohexyl-4-[4-(5-trifluoromethyl-pyridin-2-yl)-piperazine-1-carbonyl]-imidazolidin-2-one In analogy to example 1, (RS)-1-benzenesulfonyl-3-cyclohexyl-2-oxo-imidazolidine-4-carboxylic acid (example 39, step 4) was coupled with 1-[5-(trifluoromethyl)pyrid-2-yl]piperazine to give the title compound as a colorless solid. MS: 566.2 ([M+H])

Example 44

(RS)-1-Benzenesulfonyl-3-cyclohexyl-4-[4-(6-methyl-pyridin-2-yl)-piperazine-1-carbonyl]-imidazolidin-2-one In analogy to example 1, (RS)-1-benzenesulfonyl-3-cyclohexyl-2-oxo-imidazolidine-4-carboxylic acid (example 39, step 4) was coupled with 1-(2-(6-methylpyridyl)piperazine to give the title compound as a colorless solid. MS: 512.5 ([M+H]$^+$)

Example 45

(RS)-6-[4-(1-Benzenesulfonyl-3-cyclohexyl-2-oxo-imidazolidine-4-carbonyl)-piperazin-1-yl]-nicotinonitrile In analogy to example 1, (RS)-1-benzenesulfonyl-3-cyclohexyl-2-oxo-imidazolidine-4-carboxylic acid (example 39, step 4) was coupled with 6-(piperazino)pyridine-3-carbonitrile to give the title compound as a colorless solid. MS: 523.5 ([M+H]$^+$)

Example 46

(RS)-1-Benzenesulfonyl-3-cyclohexyl-4-(4-thieno[3,2-c]pyridin-4-yl-piperazine-1-carbonyl)-imidazolidin-2-one In analogy to example 1, (RS)-1-benzenesulfonyl-3-cyclohexyl-2-oxo-imidazolidine-4-carboxylic acid (example 39, step 4) was coupled with 4-piperazin-1-yl-thieno[2,3-C]pyridine to give the title compound as a colorless solid. MS: 554.2 ([M+H]$^+$)

Example 47

(RS)-1-Benzenesulfonyl-3-cyclohexyl-4-[4-(3,5-dichloro-pyridin-2-yl)-piperazine-1-carbonyl]-imidazolidin-2-one In analogy to example 1, (RS)-1-benzenesulfonyl-3-cyclohexyl-2-oxo-imidazolidine-4-carboxylic acid (example 39, step 4) was coupled with 1-(3,5-dichloro-2-pyridinyl)piperazine to give the title compound as a colorless solid. MS: 566.3 ([M+H]$^+$)

Example 48

(RS)-3-Phenyl-1-(2-trifluoromethyl-benzenesulfonyl)-4-[4-(3-trifluoromethyl-pyridin-2-yl)-piperazine-1-carbonyl]-imidazolidin-2-one In analogy to example 1, (RS)-2-oxo-3-phenyl-1-(2-trifluoromethyl-benzenesulfonyl)-imidazolidine-4-carboxylic acid (example 11) was coupled with 1-[3-(trifluoromethyl

Example 49

(RS)-1-Benzenesulfonyl-3-(2-chloro-phenyl)-4-[4-(3-trifluoromethyl-pyridin-2-yl)-piperazine-1-carbonyl]-imidazolidin-2-one Step 1: In analogy to example 1,1-benzenesulfonyl-aziridine-2-carboxylic acid methyl ester (example 39, step 2) was reacted with NaI and 2-chlorophenylisocyanate to give 1-benzenesulfonyl-3-(2-chloro-phenyl)-2-oxo-imidazolidine-4-carboxylic acid methyl ester.

Step 2: 1-Benzenesulfonyl-3-(2-chloro-phenyl)-2-oxo-imidazolidine-4-carboxylic acid methyl ester was hydrolyzed with NaOH solution to give 1-benzenesulfonyl-3-(2-chloro-phenyl)-2-oxo-imidazolidine-4-carboxylic acid.

Step 3: 1-Benzenesulfonyl-3-(2-chloro-phenyl)-2-oxo-imidazolidine-4-carboxylic acid was coupled with 1-[3-(trifluoromethyl)pyrid-2-yl]piperazine to give the title compound as a colorless solid. MS: 593.7 ([M+H]$^+$)

Example 50

(S)-1-Benzenesulfonyl-3-(2-chloro-phenyl)-4-[4-(2,5-dimethyl-phenyl)-piperazine-1-carbonyl]-imidazolidin-2-one Step 1: In analogy to example 1, L-serinemethylester hydrochloride was reacted with benzenesulfonyl chloride to give (S)-2-benzenesulfonylamino-3-hydroxy-propionic acid methyl ester.

Step 2: In analogy to example 1, (S)-2-benzenesulfonylamino-3-hydroxy-propionic acid methyl ester was treated with triphenylphosphine and DEAD to give (S)-1-benzenesulfonyl-aziridine-2-carboxylic acid methyl ester.

Steps 3-5: In analogy to example 1, (S)-1-benzenesulfonyl-aziridine-2-carboxylic acid methyl ester was reacted with NaI and 2-chlorophenyl isocyanate. The product of this reaction was hydrolyzed with NaOH solution. The product of this reaction was coupled with 1-(2,5-dimethylphenyl)piperazine to give the title compound as a colorless solid. MS: 552.7 ([M+H]$^+$)

Example 51

(RS)-4-[4-(3-Chloro-5-trifluoromethyl-pyridin-2-yl)-piperazine-1-carbonyl]-3-phenyl-1-(2-trifluoromethyl-benzenesulfonyl)-imidazolidin-2-one In analogy to example 1, (RS)-2-oxo-3-phenyl-1-(2-trifluoromethyl-benzenesulfonyl)-imidazolidine-4-carboxylic acid (example 11) was coupled with 1-[3-chloro-5-(trifluoromethyl)pyrid-2-yl]piperazine to give the title compound as a colorless solid. MS: 663.5 ([M+H])

Example 52

(RS)-1-Benzenesulfonyl-4-[4-(3-bromo-6-methyl-pyridin-2-yl)-piperazine-1-carbonyl]-3-cyclohexyl-imidazolidin-2-one Step 1: A solution of 3-bromo-2-chloro-6-picoline (0.2 g), piperazine (0.083 g) and triethylamine (0.096 g) in acetonitrile (5 ml) was heated in the microwave apparatus: 30 min at 120° C. followed by 60 min at 150° C. and 30 min at 170° C. The mixture was concentrated and the product was purified by chromatography (SiO$_2$, CH$_2$Cl$_2$=>CH$_2$Cl$_2$/CH$_3$OH 4:1) to give 1-(3-bromo-6-methyl-pyridin-2-yl)-piperazine (0.05 g) as a light yellow solid.

Step 2: In analogy to example 1, (RS)-1-benzenesulfonyl-3-cyclohexyl-2-oxo-imidazolidine-4-carboxylic acid (example 39, step 4) was coupled with 1-(3-bromo-6-methyl-pyridin-2-yl)-piperazine to give the title compound as a colorless solid. MS: 591.7 ([M+H]$^+$)

Example 53

(RS)-1-Benzenesulfonyl-3-cyclohexyl-4-[4-(4-methyl-pyridin-2-yl)-piperazine-1-carbonyl]-imidazolidin-2-one In analogy to example 1, (RS)-1-benzenesulfonyl-3-cyclohexyl-2-oxo-imidazolidine-4-carboxylic acid (example 39, step 4) was coupled with 1-(4-methyl-pyridin-2-yl)piperazine to give the title compound as a colorless solid. MS: 512.3 ([M+H]$^+$)

Example 54

(RS)-2-[4-(1-Benzenesulfonyl-3-cyclohexyl-2-oxo-imidazoldine-4-carbonyl)-piperazin-1-yl]-6-methyl-nicotinonitrile In analogy to example 1, (RS)-1-benzenesulfonyl-3-cyclohexyl-2-oxo-imidazolidine-4-carboxylic acid (example 39, step 4) was coupled with 6-methyl-2-piperazin-1-yl-nicotinonitrile (CAS 622405-21-4) to give the title compound as an off-white solid. MS: 537.0 ([M+H]$^+$)

Example 55

(RS)-1-(2,3-Dichloro-benzenesulfonyl)-4-[4-(2,5-dimethyl-phenyl)-piperazine-1-carbonyl]-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 2,3-dichlorobenzenesulfonyl chloride to give the title compound as a colorless solid. MS: 588.7 ([M+H]$^+$)

Example 56

(RS)-1-(2,5-Dichloro-benzenesulfonyl)-4-[4-(2,5-dimethyl-phenyl)-piperazine-1-carbonyl]-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 2,5-dichlorobenzenesulfonyl chloride to give the title compound as a colorless solid. MS: 588.7 ([M+H]$^+$)

Example 57

(RS)-4-[4-(2,5-Dimethyl-phenyl)-piperazine-1-carbonyl]-1-(2-fluoro-benzenesulfonyl)-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 2-fluorobenzenesulfonyl chloride to give the title compound as a colorless solid. MS: 537.0 ([M+H]$^+$)

Example 58

(RS)-4-[4-(2,5-Dimethyl-phenyl)-piperazine-1-carbonyl]-1-(3-fluoro-benzenesulfonyl)-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 3-fluorobenzenesulfonyl chloride to give the title compound as a colorless solid. MS: 537.0 ([M+H]$^+$)

Example 59

(RS)-1-(3-Chloro-2-fluoro-benzenesulfonyl)-4-[4-(2,5-dimethyl-phenyl)-piperazine-1-carbonyl]-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 3-chloro-2-fluorobenzenesulfonyl chloride to give the title compound as a colorless solid. MS: 570.8 ([M+H]$^+$)

Example 60

(RS)-1-(3-Difluoromethoxy-benzenesulfonyl)-4-[4-(2,5-dimethyl-phenyl)-piperazine-1-carbonyl]-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 3-(difluoromethoxy)benzenesulfonyl chloride to give the title compound as a colorless solid. MS: 584.7 ([M]$^+$)

Example 61

(RS)-4-[4-(2,5-Dimethyl-phenyl)-piperazine-1-carbonyl]-3-phenyl-1-(3-trifluoromethyl-benzenesulfonyl)-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 3-trifluoromethylbenzenesulphonyl chloride to give the title compound as a colorless solid. MS: 586.8 ([M+H]$^+$)

Example 62

(RS)-1-Benzenesulfonyl-3-cyclohexyl-4-(3',6'-dimethyl-2,3,5,6-tetrahydro-[1,2']bipyrazinyl-4-carbonyl)-imidazolidin-2-one In analogy to example 1, (RS)-1-benzenesulfonyl-3-cyclohexyl-2-oxo-imidazolidine-4-carboxylic acid (example 39, step 4) was coupled with 3',6'-dimethyl-3,4,5,6-tetrahydro-2H-[1,2']bipyrazinyl (CAS 59215-42-8) to give the title compound as a colorless solid. MS: 526.8 ([M+H]$^+$)

Example 63

(RS)-1-Benzenesulfonyl-3-(2-chloro-phenyl)-4-[4-(3-chloro-pyridin-2-yl)-piperazine-1-carbonyl]-imidazolidin-2-one In analogy to example 1, (RS)-1-benzenesulfonyl-3-(2-chloro-phenyl)-2-oxo-imidazolidine-4-carboxylic acid (example 49, step 2) was coupled with 1-(3-chloro-pyridin-2-yl)-piperazine hydrochloride (CAS 85386-86-3) to give the title compound as a colorless solid. MS: 560.2 ([M+H]$^+$)

Example 64

(RS)-1-(2,5-Difluoro-benzenesulfonyl)-4-[4-(2,5-dimethyl-phenyl)-piperazine-1-carbonyl]-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 2,5-difluorobenzenesulfonyl chloride to give the title compound as a colorless solid. MS: 555.3 ([M+H]$^+$)

Example 65

(RS)-1-(2,6-Dichloro-benzenesulfonyl)-4-[4-(2,5-dimethyl-phenyl)-piperazine-1-carbonyl]-3-phenyl-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and 2,6-dichlorobenzenesulfonyl chloride to give the title compound as a colorless solid. MS: 587.1 ([M+H]$^+$)

Example 66

(S)-1-Benzenesulfonyl-3-benzyl-4-[4-(2,5-dimethyl-phenyl)-piperazine-1-carbonyl]-imidazolidin-2-one Step 1: To (S)-(−)-oxo-1,5-imidazolinedicarboxylic acid 1-benzylester (10 g) and 1-(2,5-dimethylphenyl)-piperazine (7.92 g) in N,N-dimethylformamide was added O-(1,2-dihydro-2-oxo-1-pyridyl)-N,N,N,N-tetra-methyluronium-tetrafluoroborate (TPTU) (12.36 g) and triethylamine (15.8 mL), and the reaction mixture was stirred at ambient temperature over night. Additional amounts of the reagents were added, 1-(2,5-dimethylphenyl)-piperazine (1.44 g), TPTU (2.25 g) and triethylamine (2.9 mL), and stirring was continued until no starting material could be detected. The solvent was evaporated and the residue redissolved in ethyl acetate/1M aqueous solution of $Na_2CO_3$. The inorganic phase was extracted with ethyl acetate and the combined organic phases were dried ($Na_2SO_4$), filtered and evaporated. Purification by column chromatography ($SiO_2$, dichloromethane/methanol 95:5) yielded (S)-5-[4-(2,5-dimethyl-phenyl)-piperazine-1-carbonyl]-2-oxo-imidazolidine-1-carboxylic acid benzyl ester (14.4 g) as a white solid. MS: 435.3 ([M−H]$^-$)

Step 2: To a mixture of (S)-5-[4-(2,5-dimethyl-phenyl)-piperazine-1-carbonyl]-2-oxo-imidazolidine-1-carboxylic acid benzyl ester (1.0 g), N-ethyl-diisopropylamine (0.43 mL) and 4-dimethylaminopyridine (0.14 g) in dichloromethane (15 mL) was added benzenesulfonyl chloride (0.35 mL) at 0° C. The mixture was stirred at ambient temperature for 3 h, a diluted aqueous solution of $NaHCO_3$ was added, the phases were separated and the aqueous phase was extracted with ethyl acetate. The combined organic phases were dried ($Na_2SO_4$), filtered and evaporated. The crude product was purified by column chromatography ($SiO_2$, dichloromethane/methanol 98:2) to yield (S)-3-benzenesulfonyl-5-[4-(2,5-dimethyl-phenyl)-piperazine-1-carbonyl]-2-oxo-imidazolidine-1-carboxylic acid benzyl ester (1.08 g) as a white solid. MS: 576.8, ([M+H]$^+$)

Step 3: (S)-3-Benzenesulfonyl-5-[4-(2,5-dimethyl-phenyl)-piperazine-1-carbonyl]-2-oxo-imidazolidine-1-carboxylic acid benzyl ester (300 mg) in ethyl acetate (3 mL) were hydrogenated in the presence of 10% Pd/C (28 mg). After removal of the catalyst and evaporation of the solvent, the residue was purified by column chromatography (SiO$_2$, ethyl acetate) to yield (S)-1-benzenesulfonyl-4-[4-(2,5-dimethyl-phenyl)-piperazine-1-carbonyl]-imidazolidin-2-one (120 mg) as a white solid. MS: 443.4 ([M+H]$^+$)

Step 4: (S)-1-benzenesulfonyl-4-[4-(2,5-dimethyl-phenyl)-piperazine-1-carbonyl]-imidazolidin-2-one (40 mg) in acetone (5 mL) was treated with benzyl bromide (0.02 mL) and potassium carbonate (25 mg). The reaction mixture was stirred at ambient temperature overnight, additional benzyl bromide (0.03 mL) and potassium carbonate (37 mg) were added, and the mixture was heated to 70° C. for 5 h. After cooling to room temperature, ethyl acetate and a diluted aqueous solution of Na$_2$CO$_3$ were added. The phases were separated and the inorganic one was extracted with ethyl acetate. The combined organic phases were washed with brine, dried (Na$_2$SO$_4$) and evaporated. Purification by column chromatography (SiO$_2$, n-heptane/ethyl acetate 3:1 to 1:1) yielded (S)-1-benzenesulfonyl-3-benzyl-4-[4-(2,5-dimethyl-phenyl)-piperazine-1-carbonyl]-imidazolidin-2-one (41 mg) as a white solid. MS: 533.3 ([M+H]$^+$)

Example 67

(RS)-1-Benzenesulfonyl-4-(4-benzo[d]isothiazol-3-yl-piperazine-1-carbonyl)-3-(2-chloro-phenyl)-imidazolidin-2-one In analogy to example 1, (RS)-1-benzenesulfonyl-3-(2-chloro-phenyl)-2-oxo-imidazolidine-4-carboxylic acid (example 49, step 2) was coupled with 3-piperazin-1-yl-benzo[d]isothiazole hydrochloride to give the title compound as a colorless solid. MS: 581.6 ([M+H]$^+$)

Example 68

(RS)-1 Benzenesulfonyl-4-(4-benzooxazol-2-yl-piperazine-1-carbonyl)-3-(2-chloro-phenyl)-imidazolidin-2-one In analogy to example 1, (RS)-1-benzenesulfonyl-3-(2-chloro-phenyl)-2-oxo-imidazolidine-4-carboxylic acid (example 49, step 2) was coupled with 2-piperazin-1-yl-benzooxazole (CAS [111628-39-8]) to give the title compound as a colorless solid. MS: 566.3 ([M+H]$^+$)

Example 69

4-[4-(2,5-Dimethyl-phenyl)-piperazine-1-carbonyl]-3-phenyl-1-(pyridine-2-sulfonyl)-imidazolidin-2-one In analogy to example 33, (RS)-5-[4-(2,5-dimethyl-phenyl)-piperazine-1-carbonyl]-1-phenyl-imidazolidin-2-one (example 33, step 1) was reacted with sodium hydride and pyridine-2-sulfonyl chloride to give the title compound as a colorless solid. MS: 520.2 ([M+H]$^+$)

Example 70

(S)-1-(2-Chloro-benzenesulfonyl)-3-(2-chloro-phenyl)-4-[4-(2,5-dimethyl-phenyl)-piperazine-1-carbonyl]-imidazolidin-2-one Steps 1 and 2: In analogy to example 1, L-serinemethylester hydrochloride was reacted with 2-chlorophenylsulfonylchloride. Subsequent treatment with triphenylphosphine and diethylazodicarboxylate gave (S)-1-(2-chloro-benzenesulfonyl)-aziridine-2-carboxylic acid methyl ester as a light yellow oil. MS: 276.0 ([M+H]$^+$)

Step 3: In analogy to example 1, step 3, (S)-1-(2-chloro-benzenesulfonyl)-aziridine-2-carboxylic acid methyl ester was reacted with 2-chlorophenylisocyanate and sodium iodide to give (S)-1-(2-chloro-benzenesulfonyl)-3-(2-chloro-phenyl)-2-oxo-imidazolidine-4-carboxylic acid methyl ester as a colorless foam.

Steps 4 and 5: In analogy to example 1, (S)-1-(2-chloro-benzenesulfonyl)-3-(2-chloro-phenyl)-2-oxo-imidazolidine-4-carboxylic acid methyl ester was hydrolyzed using sodium hydroxide solution to give (S)-1-(2-chloro-benzenesulfonyl)-3-(2-chloro-phenyl)-2-oxo-imidazolidine-4-carboxylic acid. Finally, (S)-1-(2-chloro-benzenesulfonyl)-3-(2-chloro-phenyl)-2-oxo-imidazolidine-4-carboxylic acid was coupled with 1-(2,5-dimethylphenyl)piperazine to give the title compound as a colorless solid. MS: 587.2 ([M+H]$^+$)

Example 71

(S)-1-(2-Chloro-benzenesulfonyl)-3-(2-chloro-phenyl)-4-[4-(3-trifluoromethyl-pyridin-2-yl)-piperazine-1-carbonyl]-imidazolidin-2-one In analogy to example 1, step 5, (S)-1-(2-chloro-benzenesulfonyl)-3-(2-chloro-phenyl)-2-oxo-imidazolidine-4-carboxylic acid (example 70, step 4) was coupled with 1-[3-(trifluoromethyl)pyrid-2-yl]-piperazine to give the title compound as a colorless solid. MS: 628.3 ([M+H]$^+$)

Example 72

(S)-1-(2-Chloro-benzenesulfonyl)-3-propyl-4-[4-(3-trifluoromethyl-pyridin-2-yl)-piperazine-1-carbonyl]-imidazolidin-2-one Step 1: In analogy to example 2, L-serine was reacted with 2-chlorobenzenesulfonyl chloride to give (S)-2-(2-chloro-benzenesulfonylamino)-3-hydroxy-propionic acid as a colorless solid. MS: 278.1 ([M−H]$^-$)

Step 2: In analogy to example 2, (S)-2-(2-chloro-benzenesulfonylamino)-3-hydroxy-propionic acid was reacted with 1-[3-(trifluoromethyl)pyrid-2-yl]-piperazine to give 2-chloro-N-{(S)-1-hydroxymethyl-2-oxo-2-[4-(3-trifluoromethyl-pyridin-2-yl)-piperazin-1-yl]-ethyl}-benzenesulfonamide as a colorless foam. MS: 493.0 ([M+H]$^+$)

Step 3: In analogy to example 2,2-chloro-N-{(S)-1-hydroxymethyl-2-oxo-2-[4-(3-trifluoromethyl-pyridin-2-yl)-piperazin-1-yl]-ethyl}-benzenesulfonamide was reacted with triphenylphosphine and diethylarodicarboxylate to give [(S)-1-(2-chloro-benzenesulfonyl)-aziridin-2-yl]-[4-(3-trifluoromethyl-pyridin-2-yl)-piperazin-1-yl]-methanone as a colorless oil. MS: 475.0 ([M+H]$^+$)

Step 4: In analogy to example 2, [(S)-1-(2-chloro-benzenesulfonyl)-aziridin-2-yl]-[4-(3-trifluoromethyl-pyridin-2-yl)-piperazin-1-yl]-methanone was reacted with sodium iodide and n-propylisocyanate to give (S)-1-(2-chloro-benzenesulfonyl)-3-propyl-4-[4-(3-trifluoromethyl-pyridin-2-yl)-piperazine-1-carbonyl]-imidazolidin-2-one as a colorless foam. MS: 559.6 ([M+H]$^+$)

Example 73

1-Benzenesulfonyl-3-cyclohexyl-4-[(R)-2-methyl-4-(3-trifluoromethyl-pyridin-2-yl)-piperazine-1-carbonyl]-imidazolidin-2-one To a suspension of (RS)-1-benzenesulfonyl-3-cyclohexyl-2-oxo-imidazolidine-4-carboxylic acid (example 39, step 4, 50 mg) in toluene (0.15 ml) was added thionyl chloride (169 mg). The mixture was stirred at 75° C. for 3.5 h. The solvent was evaporated and the crude acid chloride was dissolved in dichloromethane (0.2 ml). At 0° C., (R)-3-methyl-1-(3-trifluoromethyl-pyridin-2-yl)-piperazine (42 mg) and N-ethyl-diisopropylamine (37 mg) were added. The mixture was stirred at 0° C. for 1 h and at room temperature for 1 h. The mixture was diluted with dichloromethane and washed with water. The organic phase was dried (MgSO$_4$), filtered and evaporated. The product was purified by chromatography (SiO$_2$, cyclohexane/ethyl acetate 1:0=>1:1) to give the title compound as a colorless solid. MS: 580.3 ([M+H]$^+$)

Example 74

1-Benzenesulfonyl-3-cyclohexyl-4-[(S)-2-methyl-4-(3-trifluoromethyl-pyridin-2-yl)-piperazine-1-carbonyl]-imidazolidin-2-one In analogy to example 73, (RS)-1-benzenesulfonyl-3-cyclohexyl-2-oxo-imidazolidine-4-carboxylic acid (example 39, step 4) was converted to the acid chloride and subsequently reacted with (S)-3-methyl-1-(3-trifluoromethyl-pyridin-2-yl)-piperazine to give the title compound as a colorless solid. MS: 580.3 ([M+H]$^+$)

Example 75

(S) 1-(2-Chloro-benzenesulfonyl)-3-isopropyl-4-[4-(3-trifluoromethyl-pyridin-2-yl)-piperazine-1-carbonyl]-imidazolidin-2-one In analogy to example 2, [(S)-1-(2-chloro-benzenesulfonyl)-aziridin-2-yl]-[4-(3-trifluoromethyl-pyridin-2-yl)-piperazin-1-yl]-methanone (example 72, step 3) was reacted with sodium iodide and isopropylisocyanate to give the title compound as a colorless foam. MS: 560.2 ([M+H]$^+$)

Example 76

(S)-3-Butyl-1-(2-chloro-benzenesulfonyl)-4-[4-(3-trifluoromethyl-pyridin-2-yl)-piperazine-1-carbonyl]-imidazolidin-2-one In analogy to example 2, [(S)-1-(2-chloro-benzenesulfonyl)-aziridin-2-yl]-[4-(3-trifluoromethyl-pyridin-2-yl)-piperazin-1-yl]-methanone (example 72, step 3) was reacted with sodium iodide and n-butylisocyanate to give the title compound as a colorless foam. MS: 574.2 ([M+H]$^+$)

Example 77

(S)-1-Benzenesulfonyl-4-[4-(2,5-dimethyl-phenyl)-piperazine-1-carbonyl]-3-(3-iodo-propyl)-imidazolidin-2-one In analogy to example 2, ((S)-1-benzenesulfonyl-aziridin-2-yl)-[4-(2,5-dimethyl-phenyl)-piperazin-1-yl]-methanone (example 21, step 3) was reacted with sodium iodide and 3-bromopropylisocyanate to give the title compound as a light yellow foam. MS: 610.6 ([M+H]$^+$)

Example 78

(S)-1-(2-Chloro-benzenesulfonyl)-3-cyclopropyl-4-[4-(3-trifluoromethyl-pyridin-2-yl)-piperazine-1-carbonyl]-imidazolidin-2-one In analogy to example 2, [(S)-1-(2-chloro-benzenesulfonyl)-aziridin-2-yl]-[4-(3-trifluoromethyl-pyridin-2-yl)-piperazin-1-yl]-methanone (example 72, step 3) was reacted with sodium iodide and cyclopropylisocyanate to give the title compound as a colorless foam. MS: 557.6 ([M+H]$^+$)

Example 79

(S)-1-(2-Chloro-benzenesulfonyl)-3-(tetrahydro-pyran-4-yl)-4-[4-(3-trifluoromethyl-pyridin-2-yl)-piperazine-1-carbonyl]-imidazolidin-2-one In analogy to example 2, [(S)-1-(2-chloro-benzenesulfonyl)-aziridin-2-yl]-[4-(3-trifluoromethyl-pyridin-2-yl)-piperazin-1-yl]-methanone (example 72, step 3) was reacted with sodium iodide and tetrahydropyran-4-yl-isocyanate to give the title compound as a light yellow solid. MS: 601.9 ([M+H]$^+$)

Example 80

(RS)-4-(3',6'-Dimethyl-2,3,5,6-tetrahydro-[1,2']bipyrazinyl-4-carbonyl)-3-phenyl-1-(2-trifluoromethyl-benzenesulfonyl)-imidazolidin-2-one In analogy to example 1, (RS)-2-oxo-3-phenyl-1-(2-trifluoromethyl-benzenesulfonyl)-imidazolidine-4-carboxylic acid (example 11) was coupled with 3',6'-dimethyl-3,4,5,6-tetrahydro-2H-[1,2']bipyrazinyl (CAS [59215-42-8]) to give the title compound as a colorless solid. MS: 589.0 ([M+H]$^+$)

Example 81

(RS)-1-Benzenesulfonyl-3-(2-chloro-phenyl)-4-(3',6'-dimethyl-2,3,5,6-tetrahydro-[1,2']bipyrazinyl-4-carbonyl)-imidazolidin-2-one In analogy to example 1,1-benzenesulfonyl-3-(2-chloro-phenyl)-2-oxo-imidazolidine-4-carboxylic acid (example 49, step 2) was coupled with 3',6'-dimethyl-3,4,5,6-tetrahydro-2H-[1,2']bipyrazinyl (CAS [59215-42-8]) to give the title compound as a colorless solid. MS: 555.2 ([M+H]$^+$)

Example 82

(RS)-3-(2,4-Difluoro-phenyl)-4-[4-(2,5-dimethyl-phenyl)-piperazine-1-carbonyl]-1-(propane-2-sulfonyl)-imidazolidin-2-one Step 1: To a stirred solution of aziridine-2-carboxylic acid methyl ester (0.5 g) in dichloromethane (20 ml) at 0° C. were added triethylamine (0.95 g) and isopropylsulfonyl chloride (1.38 g). The mixture was warmed to room temperature and stirred for 3.5 h. The mixture was filtered and the filtrate was concentrated. The residue was dissolved in ethyl acetate and washed with brine. The organic phase was dried (MgSO$_4$), filtered and evaporated to give the crude 1-(propane-2-sulfonyl)-aziridine-2-carboxylic acid methyl ester as a yellow oil.

Step 2: In analogy to example 1,1-(propane-2-sulfonyl)-aziridine-2-carboxylic acid methyl ester was reacted with sodium iodide and 2,4-difluorophenyl isocyanate to give (RS)-3-(2,4-difluoro-phenyl)-2-oxo-1-(propane-2-sulfonyl)-imidazolidine-4-carboxylic acid methyl ester as a colorless solid. MS: 363.3 ([M+H]$^+$)

Step 3: In analogy to example 1, (RS)-3-(2,4-difluoro-phenyl)-2-oxo-1-(propane-2-sulfonyl)-imidazolidine-4-carboxylic acid methyl ester was hydrolyzed using lithium hydroxide solution to give (RS)-3-(2,4-difluoro-phenyl)-2-oxo-1-(propane-2-sulfonyl)-imidazolidine-4-carboxylic acid.

Step 4: In analogy to example 1, (RS)-3-(2,4-difluoro-phenyl)-2-oxo-1-(propane-2-sulfonyl)-imidazolidine-4-carboxylic acid was coupled with 1-(2,5-dimethylphenyl)piperazine to give the title compound as a colorless solid. MS: 521.5 ([M+H]$^+$)

Example 83

(RS)-3-(2,4-Difluoro-phenyl)-4-(3',6'-dimethyl-2,3, 5,6-tetrahydro-[1,2']bipyrazinyl-4-carbonyl)-1-(propane-2-sulfonyl)-imidazolidin-2-one In analogy to example 1, (RS)-3-(2,4-difluoro-phenyl)-2-oxo-1-(propane-2-sulfonyl)-imidazolidine-4-carboxylic acid (example 82, step 3) was coupled with 3',6'-dimethyl-3,4,5,6-tetrahydro-2H-[1,2']bipyrazinyl (CAS [59215-42-8]) to give the title compound as a colorless solid. MS: 523.2 ([M+H]$^+$)

Example 84

(RS)-4-[4-(3-Chloro-pyridin-2-yl)-piperazine-1-carbonyl]-3-(2,4-difluoro-phenyl)-1-(propane-2-sulfonyl)-imidazolidin-2-one In analogy to example 1, (RS)-3-(2,4-difluoro-phenyl)-2-oxo-1-(propane-2-sulfonyl)-imidazolidine-4-carboxylic acid (example 82, step 3) was coupled with 1-(3-chloropyridin-2-yl)piperazine to give the title compound as a colorless solid. MS: 527.8 ([M+H]$^+$)

Example 85

(RS)-3-(2-Chloro-phenyl)-4-[4-(2,5-dimethyl-phenyl)-piperazine-1-carbonyl]-1-(propane-2-sulfonyl)-imidazolidin-2-one Step 1: In analogy to example 1, the crude 1-(propane-2-sulfonyl)-aziridine-2-carboxylic acid methyl ester from example 82, step 1 was reacted with sodium iodide and 2-chlorophenyl isocyanate to give (RS)-3-(2-chloro-phenyl)-2-oxo-1-(propane-2-sulfonyl)-imidazolidine-4-carboxylic acid methyl ester as a light yellow oil. MS: 361.1 ([M+H]$^+$)
Step 2: In analogy to example 1, (RS)-3-(2-chloro-phenyl)-2-oxo-1-(propane-2-sulfonyl)-imidazolidine-4-carboxylic acid methyl ester was hydrolyzed using lithium hydroxide solution to give (RS)-3-(2-chloro-phenyl)-2-oxo-1-(propane-2-sulfonyl)-imidazolidine-4-carboxylic acid as a colorless solid. MS: 345.0 ([M−H]$^-$)
Step 3: In analogy to example 1, (RS)-3-(2-chloro-phenyl)-2-oxo-1-(propane-2-sulfonyl)-imidazolidine-4-carboxylic acid was coupled with 1-(2,5-dimethylphenyl)piperazine to give the title compound as a colorless solid. MS: 519.3 ([M+H]$^+$)

Example 86

(RS)-3-(2-Chloro-phenyl)-4-(3',6'-dimethyl-2,3,5,6-tetrahydro-[1,2']bipyrazinyl-4-carbonyl)-1-(propane-2-sulfonyl)-imidazolidin-2-one In analogy to example 1, (RS)-3-(2-chloro-phenyl)-2-oxo-1-(propane-2-sulfonyl)-imidazolidine-4-carboxylic acid (example 85, step 2) was coupled with 3',6'-dimethyl-3,4,5,6-tetrahydro-2H-[1,2']bipyrazinyl to give the title compound as a colorless solid. MS: 521.3 ([M+H]$^+$)

Example 87

(RS)-3-(2-Chloro-phenyl)-4-[4-(3-chloro-pyridin-2-yl)-piperazine-1-carbonyl]-1-(propane-2-sulfonyl)-imidazolidin-2-one In analogy to example 1, (RS)-3-(2-chloro-phenyl)-2-oxo-1-(propane-2-sulfonyl)-imidazolidine-4-carboxylic acid (example 85, step 2) was coupled with 1-(3-chloropyridin-2-yl)piperazine to give the title compound as a colorless solid. MS: 526.3 ([M+H]$^+$)

Example 88

(S)-3-Benzyl-4-[4-(2,5-dimethyl-phenyl)-piperazine-1-carbonyl]-1-(naphthalene-1-sulfonyl)-imidazolidin-2-one Step 1: In analogy to example 66, step 2, from (S)-5-[4-(2,5-dimethyl-phenyl)-piperazine-1-carbonyl]-2-oxo-imidazolidine-1-carboxylic acid benzyl ester (example 66, step 1) and naphthalenesulfonyl chloride was prepared (S)-5-[4-(2,5-dimethyl-phenyl)-piperazine-1-carbonyl]-3-(naphthalene-1-sulfonyl)-2-oxo-imidazolidine-1-carboxylic acid benzyl ester as a white solid. MS: 627.0 ([M+H]$^+$)
Step 2: In analogy to example 66, step 3, from (S)-5-[4-(2,5-dimethyl-phenyl)-piperazine-1-carbonyl]-3-(naphthalene-1-sulfonyl)-2-oxo-imidazolidine-1-carboxylic acid benzyl ester was prepared (S)-4-[4-(2,5-dimethyl-phenyl)-piperazine-1-carbonyl]-1-(naphthalene-1-sulfonyl)-imidazolidin-2-one as a white solid. MS: 493.0 ([M+H]$^+$)
Step 3: In analogy to example 66, step 4, from (S)-4-[4-(2,5-dimethyl-phenyl)-piperazine-1-carbonyl]-1-(naphthalene-1-sulfonyl)-imidazolidin-2-one and benzyl bromide was prepared (S)-3-benzyl-4-[4-(2,5-dimethyl-phenyl)-piperazine-1-carbonyl]-1-(naphthalene-1-sulfonyl)-imidazolidin-2-one as a white solid. MS: 583.2 ([M+H]$^+$)

Example 89

(S)-4-[4-(2,5-Dimethyl-phenyl)-piperazine-1-carbonyl]-1-(naphthalene-1-sulfonyl)-3-propyl-imidazolidin-2-one In analogy to example 66, step 4, (S)-4-[4-(2,5-dimethyl-phenyl)-piperazine-1-carbonyl]-1-(naphthalene-1-sulfonyl)-imidazolidin-2-one and propyl iodide were reacted in the presence of sodium iodide in a pressure tube to yield (S)-4-[4-(2,5-dimethyl-phenyl)-piperazine-1-carbonyl]-1-(naphthalene-1-sulfonyl)-3-propyl-imidazolidin-2-one as a white solid. MS: 535.0 ([M+H])

Example 90

(S)-1-Benzenesulfonyl-4-[4-(2,5-dimethyl-phenyl)-piperazine-1-carbonyl]-3-pyridin-2-yl-imidazolidin-2-one Under argon an oven-dried flask was charged with tris (dibenzylideneacetone)dipalladium (2.5 mg), 9,9-dimethyl-4,5-bis(diphenylphosphino)xanthene (4.7 mg), cesium carbonate (41.2 mg) and dioxane (0.75 mL). The mixture was stirred for 30 min, before a mixture of (S)-1-benzenesulfonyl-4-[4-(2,5-dimethyl-phenyl)-piperazine-1-carbonyl]-imidazolidin-2-one (example 66, step 3) (40 mg) and 2-bromopyridine (17.1 mg) in dioxane (0.75 mL) was added. The reaction mixture was heated to 100° C. for 4 hours and was stirred at room temperature over night. The mixture was cooled to room temperature, an aqueous solution of NaHCO₃ was added, the phases were separated, and the inorganic one was extracted with ethyl acetate (×3). The combined organic layers were washed with brine, dried (Na₂SO₄), filtered and evaporated. Purification by chromatography (SiO₂, CH₂Cl₂/ethyl acetate 4:1 to ethyl acetate) gave (S)-1-benzenesulfonyl-4-[4-(2,5-dimethyl-phenyl)-piperazine-1-carbonyl]-3-pyridin-2-yl-imidazolidin-2-one as a light yellow solid, MS: 519.8 ([M+H]⁺).

Example 91

(S)-3-Benzyl-1-cyclopropanesulfonyl-4-[4-(2,5-dimethyl-phenyl)-piperazine-1-carbonyl]-imidazolidin-2-one Step 1: In analogy to example 66, step 2, from (S)-5-[4-(2,5-dimethyl-phenyl)-piperazine-1-carbonyl]-2-oxo-imidazolidine-1-carboxylic acid benzyl ester (example 66, step 1) and cyclopropanesulfonyl chloride was prepared (S)-3-cyclopropanesulfonyl-5-[4-(2,5-dimethyl-phenyl)-piperazine-1-carbonyl]-2-oxo-imidazolidine-1-carboxylic acid benzyl ester as a white solid. MS: 540.8 ([M+H]⁺)

Step 2: In analogy to example 66, step 3, from ((S)-3-cyclopropanesulfonyl-5-[4-(2,5-dimethyl-phenyl)-piperazine-1-carbonyl]-2-oxo-imidazolidine-1-carboxylic acid benzyl ester was prepared (S)-1-cyclopropanesulfonyl-4-[4-(2,5-dimethyl-phenyl)-piperazine-1-carbonyl]-imidazolidin-2-one as a light yellow solid. MS: 407.5 ([M+H]⁺)

Step 3: In analogy to example 66, step 4, from (S)-1-cyclopropanesulfonyl-4-[4-(2,5-dimethyl-phenyl)-piperazine-1-carbonyl]-imidazolidin-2-one and benzyl bromide was prepared
(S)-3-benzyl-1-cyclopropanesulfonyl-4-[4-(2,5-dimethyl-phenyl)-piperazine-1-carbonyl]-imidazolidin-2-one as a white solid. MS: 497.1 ([M+H]⁺)

Example 92

(S)-3-Benzyl-1-(cyclohexylmethanesulfonyl)-4-[4-(2,5-dimethyl-phenyl)-piperazine-1-carbonyl]-imidazolidin-2-one Step 1: In analogy to example 66, step 2, from (S)-5-[4-(2,5-dimethyl-phenyl)-piperazine-1-carbonyl]-2-oxo-imidazolidine-1-carboxylic acid benzyl ester (example 66, step 1) and cyclohexyl-methanesulfonyl chloride was prepared (S)-3-(cyclohexylmethanesulfonyl)-5-[4-(2,5-dimethyl-phenyl)-piperazine-1-carbonyl]-2-oxo-imidazolidine-1-carboxylic acid benzyl ester as a white solid. MS: 596.7 ([M+H]⁺)

Step 2: In analogy to example 66, step 3, from (S)-3-(cyclohexylmethanesulfonyl)-5-[4-(2,5-dimethyl-phenyl)-piperazine-1-carbonyl]-2-oxo-imidazolidine-1-carboxylic acid benzyl ester was prepared (S)-1-cyclohexylmethanesulfonyl-4-[4-(2,5-dimethyl-phenyl)-piperazine-1-carbonyl]-imidazolidin-2-one as a light yellow solid. MS: 463.1 ([M+H]⁺)

Step 3: In analogy to example 66, step 4, from (S)-1-cyclohexylmethanesulfonyl-4-[4-(2,5-dimethyl-phenyl)-piperazine-1-carbonyl]-imidazolidin-2-one and benzyl bromide was prepared (S)-3-benzyl-1-(cyclohexylmethanesulfonyl)-4-[4-(2,5-dimethyl-phenyl)-piperazine-1-carbonyl]-imidazolidin-2-one as a white solid. MS: 553.0 ([M+H]⁺)

Example 93

(S)-1-(Cyclohexylmethanesulfonyl)-4-[4-(2,5-dimethyl-phenyl)-piperazine-1-carbonyl]-3-phenyl-imidazolidin-2-one To a solution of (S)-1-cyclohexylmethanesulfonyl-4-[4-(2,5-dimethyl-phenyl)-piperazine-1-carbonyl]-imidazolidin-2-one (100 mg) in CH₂Cl₂ (3 mL) was added cupric acetate (39 mg) and triethylamine (60 µl), followed by phenyl boronic acid (53 mg). The reaction mixture was stirred at room temperature for 16 hours. Additional phenyl boronic acid (53 mg) and triethyl amine (60 µl) was added and stirring was continued for 16 hours at room temperature. The mixture was concentrated in vacuo and the residue was purified by chromatography (SiO₂, n-heptane/ethyl acetate 1:1) to give (S)-1-(cyclohexylmethanesulfonyl)-4-[4-(2,5-dimethyl-phenyl)-piperazine-1-carbonyl]-3-phenyl-imidazolidin-2-one as a white solid. MS: 539.0 ([M+H]⁺)

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesiumstearate and the flavouring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula (I):

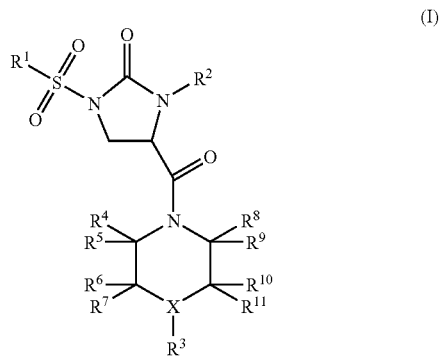

or a pharmaceutically acceptable salt thereof wherein:
X is N or CH;
$R^1$ selected from the group consisting of:
(1) lower-alkyl or fluoro-lower-alkyl,
(2) cycloalkyl or cycloalkyl-lower-alkyl,
(3) phenyl,
(4) naphthyl, and
(5) pyridinyl,
wherein said cycloalkyl, cycloalkyl-lower-alkyl, phenyl, naphthyl, or pyridinyl can optionally be substituted with 1 to 5 substituents independently selected from the group consisting of halogen, lower-alkyl, fluoro-lower-alkyl, lower-alkoxy, lower-alkoxy-lower-alkyl, and fluoro-lower-alkoxy;
$R^2$ is selected from the group consisting of:
(1) lower-alkyl or halogen-lower-alkyl,
(2) lower-alkenyl,
(3) cycloalkyl or cycloalkyl-lower-alkyl,
(4) phenyl or phenyl-lower-alkyl,
(5) naphthyl,
(6) pyridinyl, and
(7) tetrahydropyranyl,
wherein said cycloalkyl, cycloalkyl-lower-alkyl, phenyl, phenyl-lower-alkyl, naphthyl, pyridinyl or tetrahydropyranyl can optionally be substituted with 1 to 5 substituents independently selected from the group consisting of halogen, lower-alkyl, fluoro-lower-alkyl, lower-alkoxy, and fluoro-lower-alkoxy;
$R^3$ is phenyl, pyridinyl, pyrazinyl, benzo[d]isothiazolyl, benzooxazolyl, or thieno[3,2-c]pyridinyl, which can optionally be substituted with 1 to 5 substituents independently selected from the group consisting of halogen, CN, lower-alkyl, fluoro-lower-alkyl, lower-alkoxy, and fluoro-lower-alkoxy; and
$R^4$, $R^5$, $R^6$, $R^7$, $R^8$, $R^9$, $R^{10}$ and $R^{11}$ independently from each other are hydrogen or lower-alkyl.

2. A compound according to claim 1, wherein X is N.

3. A compound according to claim 1, wherein $R^1$ is lower-alkyl, fluoro-lower-alkyl or phenyl, wherein said phenyl is optionally substituted with 1 to 3 substituents independently selected from the group consisting of halogen, lower-alkyl, fluoro-lower-alkyl, lower-alkoxy and fluoro-lower-alkoxy.

4. A compound according to claim 1, wherein $R^1$ is lower-alkyl or phenyl, wherein said phenyl is optionally substituted with 1 to 2 substituents independently selected from the group consisting of halogen and fluoro-lower-alkyl.

5. A compound according to claim 1, wherein $R^1$ is isopropyl, 2-trifluoromethyl-phenyl, 2-chloro-phenyl or 2,3-dichloro-phenyl.

6. A compound according to claim 1, wherein $R^1$ is phenyl.

7. A compound according to claim 1, wherein $R^1$ is pyridinyl, naphthyl, cycloalkyl or cycloalkyl-lower-alkyl.

8. A compound according to claim 1, wherein $R^1$ is naphthyl.

9. A compound according to claim 1, wherein $R^2$ is lower-alkyl, lower-alkenyl, cycloalkyl or phenyl, wherein said phenyl is optionally substituted with 1 to 3 substituents of halogen.

10. A compound according to claim 1, wherein $R^2$ is isopropyl, cyclohexyl, phenyl, 2-fluoro-phenyl, 2-chloro-phenyl, and 2,4-difluoro-phenyl.

11. A compound according to claim 1, wherein $R^2$ is halogen-lower-alkyl, tetrahydropyranyl, pyridinyl or phenyl-lower-alkyl.

12. A compound according to claim 1, wherein $R^2$ is benzyl.

13. A compound according to claim 1, wherein $R^3$ is selected from the group consisting of phenyl, pyridinyl, thieno[3,2-c]pyridin-4-yl, and pyrazinyl; which is optionally substituted with 1 to 3 substituents independently selected from the group consisting of halogen, CN, lower-alkyl, fluoro-lower-alkyl and lower-alkoxy.

14. A compound according to claim 1, wherein $R^1$ is phenyl or pyridinyl, wherein said phenyl or pyridinyl is optionally substituted with 1 to 2 substituents independently selected from the group consisting of halogen, lower-alkyl and fluoro-lower-alkyl.

15. A compound according to claim 1, wherein $R^3$ is 2,5-dimethyl-phenyl, 2-methyl-5-chloro-phenyl, 3-trifluoromethyl-pyridin-2-yl, 3-chloro-pyridin-2-yl or 3-bromo-6-methyl-pyridin-2-yl.

16. A compound according to claim 1, wherein $R^3$ is selected from the group consisting of benzo[d]isothiazolyl, benzooxazolyl and pyrazinyl; which is optionally substituted with 1 to 3 substituents of lower-alkyl.

17. A compound according to claim 1, wherein $R^3$ is benzo[d]isothiazol-3-yl or 3,6-dimethyl-pyrazin-2-yl.

18. A compound according to claim 1, wherein $R^4$, $R^5$, $R^6$, $R^7$, $R^8$, $R^9$, $R^{10}$ and $R^{11}$ are hydrogen.

19. A compound according to claim 1 selected from the group consisting of:
(RS)-4-[4-(2,5-Dimethyl-phenyl)-piperazine-1-carbonyl]-1-(3-methoxy-benzenesulfonyl)-3-phenyl-imidazolidin-2-one,
(RS)-1-Benzenesulfonyl-4-[4-(2,5-dimethyl-phenyl)-piperazine-1-carbonyl]-3-phenyl-imidazolidin-2-one,
(RS)-1-(3-Methoxy-benzenesulfonyl)-4-[4-(2-methoxy-phenyl)-piperazine-1-carbonyl]-3-phenyl-imidazolidin-2-one,
(RS)-1-(3-Methoxy-benzenesulfonyl)-3-phenyl-4-[4-(3-trifluoromethyl-phenyl)-piperazine-1-carbonyl]-imidazolidin-2-one,
(RS)-1-(3-Methoxy-benzenesulfonyl)-3-phenyl-4-[4-(3-trifluoromethyl-pyridin-2-yl)-piperazine-1-carbonyl]-imidazolidin-2-one,
(RS)-1-(3-Methoxy-benzenesulfonyl)-4-[4-(3-methyl-pyridin-2-yl)-piperazine-1-carbonyl]-3-phenyl-imidazolidin-2-one,
(RS)-1-(3-Methoxy-benzenesulfonyl)-4-[4-(2-methoxy-phenyl)-piperidine-1-carbonyl]-3-phenyl-imidazolidin-2-one,
(RS)-3-(2-Chloro-phenyl)-4-[4-(2,5-dimethyl-phenyl)-piperazine-1-carbonyl]-1-(3-methoxy-benzenesulfonyl)-imidazolidin-2-one,
(RS)-4-[4-(5-Chloro-2-methyl-phenyl)-piperazine-1-carbonyl]-3-(2-chloro-phenyl)-1-(3-methoxy-benzenesulfonyl)-imidazolidin-2-one,
(RS)-4-[4-(2,5-Dimethyl-phenyl)-piperazine-1-carbonyl]-3-phenyl-1-(toluene-4-sulfonyl)-imidazolidin-2-one,
(RS)-4-[4-(2,5-Dimethyl-phenyl)-piperazine-1-carbonyl]-3-phenyl-1-(2-trifluoromethyl-benzenesulfonyl)-imidazolidin-2-one,
(RS)-4-[4-(5-Chloro-2-methyl-phenyl)-piperazine-1-carbonyl]-3-phenyl-1-(2-trifluoromethyl-benzenesulfonyl)-imidazolidin-2-one,
(RS)-2-{4-[2-Oxo-3-phenyl-1-(2-trifluoromethyl-benzenesulfonyl)-imidazolidine-4-carbonyl]-piperazin-1-yl}-benzonitrile,
(RS)-1-Benzenesulfonyl-4-[4-(2,5-dimethyl-phenyl)-piperazine-1-carbonyl]-3-ethyl-imidazolidin-2-one,
(RS)-1-Benzenesulfonyl-4-[4-(2,5-dimethyl-phenyl)-piperazine-1-carbonyl]-3-isopropyl-imidazolidin-2-one,
(RS)-1-Benzenesulfonyl-4-[4-(2,5-dimethyl-phenyl)-piperazine-1-carbonyl]-3-propyl-imidazolidin-2-one,
(RS)-3-Allyl-1-benzenesulfonyl-4-[4-(2,5-dimethyl-phenyl)-piperazine-1-carbonyl]-imidazolidin-2-one,
(RS)-1-Benzenesulfonyl-3-butyl-4-[4-(2,5-dimethyl-phenyl)-piperazine-1-carbonyl]-imidazolidin-2-one,
(RS)-1-Benzenesulfonyl-3-cyclopentyl-4-[4-(2,5-dimethyl-phenyl)-piperazine-1-carbonyl]-imidazolidin-2-one,
(RS)-1-Benzenesulfonyl-3-cyclohexyl-4-[4-(2,5-dimethyl-phenyl)-piperazine-1-carbonyl]-imidazolidin-2-one,
(S)-1-Benzenesulfonyl-4-[4-(2,5-dimethyl-phenyl)-piperazine-1-carbonyl]-3-phenyl-imidazolidin-2-one,
(R)-1-Benzenesulfonyl-4-[4-(2,5-dimethyl-phenyl)-piperazine-1-carbonyl]-3-phenyl-imidazolidin-2-one,
(S)-1-Benzenesulfonyl-4-[4-(2,5-dimethyl-phenyl)-piperazine-1-carbonyl]-3-(2-fluoro-phenyl)-imidazolidin-2-one,
(RS)-1-Benzenesulfonyl-3-(2-chloro-phenyl)-4-[4-(2,5-dimethyl-phenyl)-piperazine-1-carbonyl]-imidazolidin-2-one,
(RS)-1-Benzenesulfonyl-3-(3-chloro-phenyl)-4-[4-(2,5-dimethyl-phenyl)-piperazine-1-carbonyl]-imidazolidin-2-one,
(RS)-1-Benzenesulfonyl-3-(4-chloro-phenyl)-4-[4-(2,5-dimethyl-phenyl)-piperazine-1-carbonyl]-imidazolidin-2-one,
(RS)-1-Benzenesulfonyl-4-[4-(2,5-dimethyl-phenyl)-piperazine-1-carbonyl]-3-(4-fluoro-phenyl)-imidazolidin-2-one,
(S)-1-Benzenesulfonyl-4-[4-(2,5-dimethyl-phenyl)-piperazine-1-carbonyl]-3-(4-fluoro-phenyl)-imidazolidin-2-one,
(S)-1-Benzenesulfonyl-3-(2,4-difluoro-phenyl)-4-[4-(2,5-dimethyl-phenyl)-piperazine-1-carbonyl]-imidazolidin-2-one,
(RS)-1-Benzenesulfonyl-3-benzyl-4-[4-(2,5-dimethyl-phenyl)-piperazine-1-carbonyl]-imidazolidin-2-one,
(+)-4-[4-(5-Chloro-2-methyl-phenyl)-piperazine-1-carbonyl]-3-(2-chloro-phenyl)-1-(3-methoxy-benzenesulfonyl)-imidazolidin-2-one,
(−)-4-[4-(5-Chloro-2-methyl-phenyl)-piperazine-1-carbonyl]-3-(2-chloro-phenyl)-1-(3-methoxy-benzenesulfonyl)-imidazolidin-2-one, (RS)-1-(3-Chloro-benzenesulfonyl)-4-[4-(2,5-dimethyl-phenyl)-piperazine-1-carbonyl]-3-phenyl-imidazolidin-2-one, (RS)-1-(2-Chloro-benzenesulfonyl)-4-[4-(2,5-dimethyl-phenyl)-piperazine-1-carbonyl]-3-phenyl-imidazolidin-2-one, and any pharmaceutically acceptable salt thereof.

20. A compound according to claim 1 selected from the group consisting of:

(RS)-1-(2,4-Difluoro-benzenesulfonyl)-4-[4-(2,5-dimethyl-phenyl)-piperazine-1-carbonyl]-3-phenyl-imidazolidin-2-one, (RS)-4-[4-(2,5-Dimethyl-phenyl)-piperazine-1-carbonyl]-3-phenyl-1-(3,3,3-trifluoro-propane-1-sulfonyl)-imidazolidin-2-one, (RS)-4-[4-(2,5-Dimethyl-phenyl)-piperazine-1-carbonyl]-3-phenyl-1-(propane-2-sulfonyl)-imidazolidin-2-one, (RS)-1-(Butane-1-sulfonyl)-4-[4-(2,5-dimethyl-phenyl)-piperazine-1-carbonyl]-3-phenyl-imidazolidin-2-one, (RS)-1-Benzenesulfonyl-3-cyclohexyl-4-[4-(3-trifluoromethyl-pyridin-2-yl)-piperazine-1-carbonyl]-imidazolidin-2-one, (RS)-1-Benzenesulfonyl-4-[4-(3-chloro-5-trifluoromethyl-pyridin-2-yl)-piperazine-1-carbonyl]-3-cyclohexyl-imidazolidin-2-one, (RS)-2-[4-(1-Benzenesulfonyl-3-cyclohexyl-2-oxo-imidazolidine-4-carbonyl)-piperazin-1-yl]-nicotinonitrile, (RS)-1-Benzenesulfonyl-3-cyclohexyl-4-(4-pyridin-2-yl-piperazine-1-carbonyl)-imidazolidin-2-one, (RS)-1-Benzenesulfonyl-3-cyclohexyl-4-[4-(5-trifluoromethyl-pyridin-2-yl)-piperazine-1-carbonyl]-imidazolidin-2-one, (RS)-1-Benzenesulfonyl-3-cyclohexyl-4-[4-(6-methyl-pyridin-2-yl)-piperazine-1-carbonyl]-imidazolidin-2-one, (RS)-6-[4-(1-Benzenesulfonyl-3-cyclohexyl-2-oxo-imidazolidine-4-carbonyl)-piperazin-1-yl]-nicotinonitrile, (RS)-1-Benzenesulfonyl-3-cyclohexyl-4-(4-thieno[3,2-c]pyridin-4-yl-piperazine-1-carbonyl)-imidazolidin-2-one, (RS)-1-Benzenesulfonyl-3-cyclohexyl-4-[4-(3,5-dichloro-pyridin-2-yl)-piperazine-1-carbonyl]-imidazolidin-2-one, (RS)-3-Phenyl-1-(2-trifluoromethyl-benzenesulfonyl)-4-[4-(3-trifluoromethyl-pyridin-2-yl)-piperazine-1-carbonyl]-imidazolidin-2-one, (RS)-1-Benzenesulfonyl-3-(2-chloro-phenyl)-4-[4-(3-trifluoromethyl-pyridin-2-yl)-piperazine-1-carbonyl]-imidazolidin-2-one, (S)-1-Benzenesulfonyl-3-(2-chloro-phenyl)-4-[4-(2,5-dimethyl-phenyl)-piperazine-1-carbonyl]-imidazolidin-2-one, (RS)-4-[4-(3-Chloro-5-trifluoromethyl-pyridin-2-yl)-piperazine-1-carbonyl]-3-phenyl-1-(2-trifluoromethyl-benzenesulfonyl)-imidazolidin-2-one, (RS)-1-Benzenesulfonyl-4-[4-(3-bromo-6-methyl-pyridin-2-yl)-piperazine-1-carbonyl]-3-cyclohexyl-imidazolidin-2-one, (RS)-1-Benzenesulfonyl-3-cyclohexyl-4-[4-(4-methyl-pyridin-2-yl)-piperazine-1-carbonyl]-imidazolidin-2-one, (RS)-2-[4-(1-Benzenesulfonyl-3-cyclohexyl-2-oxo-imidazolidine-4-carbonyl)-piperazin-1-yl]-6-methyl-nicotinonitrile, (RS)-1-(2,3-Dichloro-benzenesulfonyl)-4-[4-(2,5-dimethyl-phenyl)-piperazine-1-carbonyl]-3-phenyl-imidazolidin-2-one, (RS)-1-(2,5-Dichloro-benzenesulfonyl)-4-[4-(2,5-dimethyl-phenyl)-piperazine-1-carbonyl]-3-phenyl-imidazolidin-2-one, (RS)-4-[4-(2,5-Dimethyl-phenyl)-piperazine-1-carbonyl]-1-(2-fluoro-benzenesulfonyl)-3-phenyl-imidazolidin-2-one, (RS)-4-[4-(2,5-Dimethyl-phenyl)-piperazine-1-carbonyl]-1-(3-fluoro-benzenesulfonyl)-3-phenyl-imidazolidin-2-one, (RS)-1-(3-Chloro-2-fluoro-benzenesulfonyl)-4-[4-(2,5-dimethyl-phenyl)-piperazine-1-carbonyl]-3-phenyl-imidazolidin-2-one, (RS)-1-(3-Difluoromethoxy-benzenesulfonyl)-4-[4-(2,5-dimethyl-phenyl)-piperazine-1-carbonyl]-3-phenyl-imidazolidin-2-one, (RS)-4-[4-(2,5-Dimethyl-phenyl)-piperazine-1-carbonyl]-3-phenyl-1-(3-trifluoromethyl-benzenesulfonyl)-imidazolidin-2-one, (RS)-1-Benzenesulfonyl-3-cyclohexyl-4-(3',6'-dimethyl-2,3,5,6-tetrahydro-[1,2']bipyrazinyl-4-carbonyl)-imidazolidin-2-one, (RS)-1-Benzenesulfonyl-3-(2-chloro-phenyl)-4-[4-(3-chloro-pyridin-2-yl)-piperazine-1-carbonyl]-imidazolidin-2-one, (RS)-1-(2,5-Difluoro-benzenesulfonyl)-4-[4-(2,5-dimethyl-phenyl)-piperazine-1-carbonyl]-3-phenyl-imidazolidin-2-one, (RS)-1-(2,6-Dichloro-benzenesulfonyl)-4-[4-(2,5-dimethyl-phenyl)-piperazine-1-carbonyl]-3-phenyl-imidazolidin-2-one, (S)-1-benzenesulfonyl-3-benzyl-4-[4-(2,5-dimethyl-phenyl)-piperazine-1-carbonyl]-imidazolidin-2-one, and any pharmaceutically acceptable salt thereof.

21. A compound according to claim 1 selected from the group consisting of:

(RS)-4-[4-(2,5-Dimethyl-phenyl)-piperazine-1-carbonyl]-3-phenyl-1-(2-trifluoromethyl-benzenesulfonyl)-imidazolidin-2-one, (RS)-4-[4-(5-Chloro-2-methyl-phenyl)-piperazine-1-carbonyl]-3-phenyl-1-(2-trifluoromethyl-benzenesulfonyl)-imidazolidin-2-one, (RS)-1-Benzenesulfonyl-4-[4-(2,5-dimethyl-phenyl)-piperazine-1-carbonyl]-3-isopropyl-imidazolidin-2-one, (S)-1-Benzenesulfonyl-4-[4-(2,5-dimethyl-phenyl)-piperazine-1-carbonyl]-3-(2-fluoro-phenyl)-imidazolidin-2-one, (S)-1-Benzenesulfonyl-3-(2,4-difluoro-phenyl)-4-[4-(2,5-dimethyl-phenyl)-piperazine-1-carbonyl]-imidazolidin-2-one, (RS)-1-(2-Chloro-benzenesulfonyl)-4-[4-(2,5-dimethyl-phenyl)-piperazine-1-carbonyl]-3-phenyl-imidazolidin-2-one, (RS)-4-[4-(2,5-Dimethyl-phenyl)-piperazine-1-carbonyl]-3-phenyl-1-(propane-2-sulfonyl)-imidazolidin-2-one, (RS)-1-Benzenesulfonyl-3-cyclohexyl-4-[4-(3-trifluoromethyl-pyridin-2-yl)-piperazine-1-carbonyl]-imidazolidin-2-one, (RS)-1-Benzenesulfonyl-3-(2-chloro-phenyl)-4-[4-(3-trifluoromethyl-pyridin-2-yl)-piperazine-1-carbonyl]-imidazolidin-2-one, (S)-1-Benzenesulfonyl-3-(2-chloro-phenyl)-4-[4-(2,5-dimethyl-phenyl)-piperazine-1-carbonyl]-imidazolidin-2-one, (RS)-1-Benzenesulfonyl-4-[4-(3-bromo-6-methyl-pyridin-2-yl)-piperazine-1-carbonyl]-3-cyclohexyl-imidazolidin-2-one, (RS)-1-(2,3-Dichloro-benzenesulfonyl)-4-[4-(2,5-dimethyl-phenyl)-piperazine-1-carbonyl]-3-phenyl-imidazolidin-2-one, (RS)-1-Benzenesulfonyl-3-(2-chloro-phenyl)-4-[4-(3-chloro-pyridin-2-yl)-piperazine-1-carbonyl]-imidazolidin-2-one, and any pharmaceutically acceptable salt thereof.

22. A compound according to claim 1 selected from the group consisting of:

(RS)-1-Benzenesulfonyl-4-(4-benzo[d]isothiazol-3-yl-piperazine-1-carbonyl)-3-(2-chloro-phenyl)-imidazolidin-2-one, (RS)-1-Benzenesulfonyl-4-(4-benzooxazol-2-yl-piperazine-1-carbonyl)-3-(2-chloro-phenyl)-imidazolidin-2-one, 4-[4-(2,5-Dimethyl-phenyl)-piperazine-1-carbonyl]-3-phenyl-1-(pyridine-2-sulfonyl)-imidazolidin-2-one, (S)-1-(2-Chloro-benzenesulfonyl)-3-(2-chloro-phenyl)-4-[4-(2,5-dimethyl-phenyl)-piperazine-1-carbonyl]-imidazolidin-2-one, (S)-1-(2-Chloro-benzenesulfonyl)-3-(2-chloro-phenyl)-4-[4-(3-trifluoromethyl-pyridin-2-yl)-piperazine-1-carbonyl]-imidazolidin-2-one, (S)-1-(2-Chloro-benzenesulfonyl)-3-propyl-4-[4-(3-trifluoromethyl-pyridin-2-yl)-piperazine-1-carbonyl]-imidazolidin-2-one, 1-Benzenesulfonyl-3-cyclohexyl-4-[(R)-2-methyl-4-(3-trifluoromethyl-pyridin-2-yl)-piperazine-1-carbonyl]-imidazolidin-2-one, 1-Benzenesulfonyl-3-cyclohexyl-4-[(S)-2-methyl-4-(3-trifluoromethyl-pyridin-2-yl)-piperazine-1-carbonyl]-imidazolidin-2-one, (S)-1-(2-Chloro-benzenesulfonyl)-3-isopropyl-4-[4-(3-trifluoromethyl-pyridin-2-yl)-piperazine-1-carbonyl]-imidazolidin-2-one, (S)-3-Butyl-1-(2-chloro-benzenesulfonyl)-4-[4-(3-trifluoromethyl-pyridin-2-yl)-piperazine-1-carbonyl]-imidazolidin-2-one, (S)-1-Benzenesulfonyl-4-[4-(2,5-dimethyl-phenyl)-piperazine-1-carbonyl]-3-(3-iodo-propyl)-imidazolidin-2-one, (S)-1-(2-Chloro-benzenesulfonyl)-3-cyclopropyl-4-[4-(3-trifluoromethyl-pyridin-2-yl)-piperazine-1-carbonyl]-imidazolidin-2-one, (S)-1-(2-Chloro-benzenesulfonyl)-3-(tetrahydro-pyran-4-yl)-4-[4-(3-trifluoromethyl-pyridin-2-yl)-piperazine-1-carbonyl]-imidazolidin-2-one, (RS)-4-(3',6'-Dimethyl-2,3,5,6-tetrahydro-[1,2']bipyrazinyl-4-carbonyl)-3-phenyl-1-(2-trifluoromethyl-benzenesulfonyl)-imidazolidin-2-one, (RS)-1-Benzenesulfonyl-3-(2-chloro-phenyl)-4-(3',6'-dimethyl-2,3,5,6-tetrahydro-[1,2']bipyrazinyl-4-carbonyl)-imidazolidin-2-one, (RS)-3-(2,4-Difluoro-phenyl)-4-[4-(2,5-dimethyl-phenyl)-piperazine-1-carbonyl]-1-(propane-2-sulfonyl)-imidazolidin-2-one, (RS)-3-(2,4-Difluoro-phenyl)-4-(3',6'-dimethyl-2,3,5,6-tetrahydro-[1,2']bipyrazinyl-4-carbonyl)-1-(propane-2-sulfonyl)-imidazolidin-2-one, (RS)-4-[4-(3-Chloro-pyridin-2-yl)-piperazine-1-carbonyl]-3-(2,4-difluoro-phenyl)-1-(propane-2-sulfonyl)-imidazolidin-2-one, (RS)-3-(2-Chloro-phenyl)-4-[4-(2,5-dimethyl-phenyl)-piperazine-1-carbonyl]-1-(propane-2-sulfonyl)-imidazolidin-2-one, (RS)-3-(2-Chloro-phenyl)-4-(3',6'-dimethyl-2,3,5,6-tetrahydro-[1,2']bipyrazinyl-4-carbonyl)-1-(propane-2-sulfonyl)-imidazolidin-2-one, (RS)-3-(2-Chloro-phenyl)-4-[4-(3-chloro-pyridin-2-yl)-piperazine-1-carbonyl]-1-(propane-2-sulfonyl)-imidazolidin-2-one, (S)-3-Benzyl-4-[4-(2,5-dimethyl-phenyl)-piperazine-1-carbonyl]-1-(naphthalene-1-sulfonyl)-imidazolidin-2-one, (S)-4-[4-(2,5-Dimethyl-phenyl)-piperazine-1-carbonyl]-1-(naphthalene-1-sulfonyl)-3-propyl-imidazolidin-2-one, (S)-1-Benzenesulfonyl-4-[4-(2,5-dimethyl-phenyl)-piperazine-1-carbonyl]-3-pyridin-2-yl-imidazolidin-2-one, (S)-3-Benzyl-1-cyclopropanesulfonyl-4-[4-(2,5-dimethyl-phenyl)-piperazine-1-carbonyl]-imidazolidin-2-one, (S)-3-Benzyl-1-(cyclohexylmethanesulfonyl)-4-[4-(2,5-dimethyl-phenyl)-piperazine-1-carbonyl]-imidazolidin-2-one, (S)-1-(Cyclohexylmethanesulfonyl)-4-[4-(2,5-dimethyl-phenyl)-piperazine-1-carbonyl]-3-phenyl-imidazolidin-2-one, and any pharmaceutically acceptable salt thereof.

23. A compound according claim 1 selected from the group consisting of:

(RS)-1-Benzenesulfonyl-4-(4-benzo[d]isothiazol-3-yl-piperazine-1-carbonyl)-3-(2-chloro-phenyl)-imidazolidin-2-one, (S)-1-(2-Chloro-benzenesulfonyl)-3-(2-chloro-phenyl)-4-[4-(2,5-dimethyl-phenyl)-piperazine-1-carbonyl]-imidazolidin-2-one, (S)-1-(2-Chloro-benzenesulfonyl)-3-(2-chloro-phenyl)-4-[4-(3-trifluoromethyl-pyridin-2-yl)-piperazine-1-carbonyl]-imidazolidin-2-one, (RS)-4-(3',6'-Dimethyl-2,3,5,6-tetrahydro-[1,2']bipyrazinyl-4-carbonyl)-3-phenyl-1-(2-trifluoromethyl-benzenesulfonyl)-imidazolidin-2-one, (RS)-3-(2-Chloro-phenyl)-4-[4-(2,5-dimethyl-phenyl)-piperazine-1-carbonyl]-1-(propane-2-sulfonyl)-imidazolidin-2-one, (S)-3-Benzyl-4-[4-(2,5-dimethyl-phenyl)-piperazine-1-carbonyl]-1-(naphthalene-1-sulfonyl)-imidazolidin-2-one, and any pharmaceutically acceptable salt thereof.

24. A pharmaceutical composition comprising a therapeutically effective amount of a compound of claim 1 and a pharmaceutically acceptable carrier.

* * * * *

UNITED STATES PATENT AND TRADEMARK OFFICE
CERTIFICATE OF CORRECTION

PATENT NO. : 7,625,902 B2 Page 1 of 1
APPLICATION NO. : 12/053674
DATED : December 1, 2009
INVENTOR(S) : H. Dehmlow et al.

It is certified that error appears in the above-identified patent and that said Letters Patent is hereby corrected as shown below:

Claim 14, column 49, line 29, delete "R1" and insert -- $R^3$ --.

Signed and Sealed this

Sixteenth Day of March, 2010

David J. Kappos
*Director of the United States Patent and Trademark Office*